United States Patent
Stegmann et al.

(10) Patent No.: US 8,983,570 B2
(45) Date of Patent: Mar. 17, 2015

(54) THERAPEUTIC ANGIOGENESIS FOR TREATMENT OF THE SPINE

(75) Inventors: Thomas J. Stegmann, Petersberg (DE); Kenneth A. Thomas, Chatham, NJ (US); John W. Jacobs, Amarillo, TX (US); Tugan Muftuler, Aliso Viejo, CA (US); Shadfar Bahri, Irvine, CA (US); Hon Yu, Irvine, CA (US); Vance Gardner, Irvine, CA (US)

(73) Assignee: Cardiovascular Biotherapeutics, Inc., Las Vegas, NV (US)

( * ) Notice: Subject to any disclaimer, the term of this patent is extended or adjusted under 35 U.S.C. 154(b) by 1362 days.

(21) Appl. No.: 12/076,846

(22) Filed: Mar. 24, 2008

(65) Prior Publication Data

US 2009/0076481 A1    Mar. 19, 2009

Related U.S. Application Data

(60) Provisional application No. 60/920,254, filed on Mar. 27, 2007, provisional application No. 61/022,266, filed on Jan. 18, 2008.

(51) Int. Cl.
| | |
|---|---|
| *A61B 5/05* | (2006.01) |
| *G01N 33/74* | (2006.01) |
| *G01N 33/84* | (2006.01) |
| *A61K 38/17* | (2006.01) |
| *A61K 38/18* | (2006.01) |

(52) U.S. Cl.
CPC .............. *G01N 33/74* (2013.01); *G01N 33/84* (2013.01); *A61K 38/1709* (2013.01); *A61K 38/1825* (2013.01); *G01N 2333/50* (2013.01); *G01N 2333/96486* (2013.01); *G01N 2800/10* (2013.01); *G01N 2800/105* (2013.01)

USPC ........... 600/407; 600/300; 600/309; 600/310; 600/314; 600/363; 600/504; 600/594; 600/420; 600/410; 600/411; 600/419

(58) Field of Classification Search
USPC ......... 600/300, 309, 310, 314, 363, 504, 594, 600/407, 410, 411, 419, 420
See application file for complete search history.

(56) References Cited

U.S. PATENT DOCUMENTS

| | | | |
|---|---|---|---|
| 6,933,286 B2 | 8/2005 | Emanuele | |
| 2002/0122792 A1* | 9/2002 | Stegmann | 424/94.1 |
| 2002/0155532 A1* | 10/2002 | Stegmann et al. | 435/69.1 |
| 2003/0103943 A1* | 6/2003 | Rosengart et al. | 424/93.2 |
| 2003/0165473 A1* | 9/2003 | Masuda et al. | 424/93.7 |

(Continued)

OTHER PUBLICATIONS

Bydder, G.M., New Approaches to Magnetic Resonance Imaging of Intervertebral Discs, Tendons, Ligaments, and Menisci, 2002, Spine, vol. 27, No. 12, pp. 1264-1268.*

(Continued)

*Primary Examiner* — Melanie Y Brown
*Assistant Examiner* — Erik B Crawford
(74) *Attorney, Agent, or Firm* — Brainspark Associates, LLC

(57) ABSTRACT

The invention relates to methods for the diagnosis, amelioration, and treatment of back pain, particularly lumbar back pain, in particular, back pain caused by muscular abnormalities, vertebral body osteoporosis, and disc degeneration. Patients with back pain are categorized into specific subsets that are deemed to have potential to respond to therapy. In particular, the invention includes a therapy involving stimulation of neovascularization so as to increase perfusion of various spine compartments.

20 Claims, 6 Drawing Sheets

Abnormal MRA Scan    Grade 1 DDD    Perfusion ($K^{trans}$)    $K^{trans}$

(56) References Cited

U.S. PATENT DOCUMENTS

2004/0052829 A1* 3/2004 Shimp .................... 424/423
2007/0255130 A1* 11/2007 Du .......................... 600/410

OTHER PUBLICATIONS

Urban, J.P.G. and Winlove, C.P., Pathophysiology of the Intervertebral Disc and the Challenges for MRI, 2007, J. Magn. Reson. Imaging, vol. 25, pp. 429-432.*
Fingl, E. et al., "General Principles," The Pharmacological Basis of Therapeutics, pp. 1-46 (1975).
Frymoyer, J.W. et al., "The Economics of Spinal Disorders," The Adult Spine: Principles and Practice, pp. 143-150 (2nd ed. 1997).
Nagase, H. et al., The Journal of Biological Chemistry, vol. 274(31), pp. 21491-21494 (1999).
Crock, H.V., "The Practice of Spinal Surgery", Springer-Verlag, pp. 35-92 (1983).
Frymoyer, J.W. et al., "Chapter 8: The Economics of Spinal Disorders," The Adult Spine: Principles and Practice, pp. 143-150 (2nd ed. 1997), Lippincott-Raven Publishers, U.S. Publication.
Lively, M.W., "Sports Medicine Approach to Low Back Pain," Southern Medical Journal, vol. 95(6), pp. 642-646 (2002), Lippincott Williams & Wilkins, U.S. Publication.
Hart, L. et al., "Physician Office Visits for Low Back Pain—Frequency, Clinical Evaluation, and Treatment Patterns from a U.S. National Survey," Spine, vol. 20(1), pp. 11-19 (1995), J.B. Lippincott Company, U.S. Publication.
Horner, H.A. et al., "2001 Volvo Award Winner in Basic Science Studies: Effect of Nutrient Supply on the Viability of Cells From the Nucleus Pulposus of the Intervertebral Disc," Spine, vol. 26(23), pp. 2543-2549 (2001), Lippincott Williams & Wilkins, Inc., U.S. Publication.
Kauppila, L. et al., "Disc Degeneration/Back Pain and Calcification of the Abdominal Aorta: A 25-Year Follow-Up Study in Framingham," Spine, vol. 22(14), pp. 1642-1649 (Jul. 1997), Lippincott-Raven Publishers, U.S. Publication.
Kurunlahti, M. et al., "Correlation of Diffusion in Lumbar Intervertebral Disks with Occlusion of Lumbar Arteries: A Study in Adult Volunteers," Radiology, vol. 221, pp. 779-786 (2001), Radiological Society of North America, Inc., U.S. Publication.
Iwahashi, M. et al., "Mechanism of Intervertebral Disc Degeneration Caused by Nicotine in Rabbits to Explicate Intervertebral Disc Disorders Caused by Smoking," Spine, vol. 27(13), pp. 1396-1401 (2002), Lippincott Williams & Wilkins, Inc., U.S. Publication.
Boos, N. et al., "Classificiation of Age-Related Changes in Lumbar Intervertebral Discs," Spine, vol. 27(23), pp. 2631-2644 (2002), U.S. Publication.
Rajasekaran, S. et al., "ISSLS Prize Winner: A Study of Diffusion in Human Lumbar Discs: A Serial Magnetic Resonance Imaging Study Documenting the Influence of the Endplate on Diffusion in Normal and Degenerate Discs," Spine, vol. 29(23), pp. 2654-2667 (2004), Lippincott Williams & Wilkins, Inc., U.S. Publication.
Levicoff, E.A. et al., "Gene Therapy for Disc Repair," The Spine Journal, vol. 5, pp. 287S-296S (2005), Elsevier, U.S. Publication.
Yoon, S.T., "Molecular Therapy of the Intervertebral Disc," The Spine Journal, vol. 5, pp. 280S-286S (2005), Elsevier, U.S. Publication.
Masuda, K. et al., "Growth Factors and Treatment of Intervertebral Disc Degeneration," Spine, vol. 29(23), pp. 2757-2769 (2004), Lippincott Williams & Wilkins, Inc., U.S. Publication.
Shimer, A.L. et al., "Gene Therapy Approaches for Intervertebral Disc Degeneration," Spine, vol. 29(23), pp. 2770-2778 (2004), Lippincott Williams & Wilkins Inc., U.S. Publication.
Setton, L.A. et al., "Cell Mechanics and Mechanobiology in the Intervertebral Disc," Spine, vol. 29(23), pp. 2710-2723 (2004), Lippincott Williams & Wilkins Inc., U.S. Publication.
Roughley, P.J., "Biology of Intervertebral Disc Aging and Degeneration," Spine, vol. 29(23), pp. 2691-2699 (2004), Lippincott Williams & Wilkins Inc., U.S. Publication.
Roberts, S. et al., "Matrix Metalloproteinases and Aggrecanase—Their Role in Disorders of the Human Intervertebral Disc," Spine, vol. 25(23), pp. 3005-3013 (2000), Lippincott Williams & Wilkins Inc., U.S. Publication.
Nagase, H. et al., "Matrix Metalloproteinases," The Journal of Biological Chemistry, vol. 274(31), pp. 21491-21494 (1999), The American Society for Biochemistry and Molecular Biology Inc., U.S. Publication.
Wallach, C.J. et al., "Gene Transfer of the Catabolic Inhibitor TIMP-1 Increases Measured Proteoglycans in Cells from Degeneration Human Intervertebral Discs," Spine, vol. 28(20), pp. 2331-2337 (2003), Lippincott Williams & Wilkins Inc., U.S. Publication.
Thompson, J.P. et al., "Stimulation of Mature Canine Intervertebral Disc by Growth Factors," Spine, vol. 16(3), pp. 253-260 (1991), Lippincott-Raven Publishers, U.S. Publication.
Yoon, S.T. et al., "ISSLS Prize Winner: LMP-1 Upregulates Intervertebral Disc Cell Production of Proteoglycans and BMPs In Vitro and In Vivo," Spine, vol. 29(23), pp. 2603-2611 (2004), Lippincott Williams & Wilkins Inc., U.S. Publication.
Kim, K.S. et al., "Inhibition of Proteoglycan and Type II Collagen Synthesis of Disc Nucleus Cells by Nicotine," Journal of Neurosurgery: Spine, vol. 99(3), pp. 291-297 (2003), American Association of Neurosurgeons, U.S. Publication.
Masuda, K. et al., "Recombinant Osteogenic Protein-1 Upregulates Extracellular Matrix Metabolism by Rabbit Annulus Fibrosus and Nucleus Pulposus Cells Cultured in Alginate Beads," Journal of Orthopaedic Research., vol. 21, pp. 922-930 (2003), Elsevier, U.S. Publication.
Zhang, Y. et al., "Growth Factor Osteogenic Protein-1—Differing Effects of Cells from Three Distinct Zones in the Bovine Intervertebral Disc," American Journal of Physical Medicine and Rehabilitation, vol. 83(7), pp. 515-521 (2004), Lippincott Williams & Wilkins Inc., U.S. Publication.
Takegami, K. et al., "Osteogenic Protein-1 Enhances Matrix Replenishment by Intervertebral Disc Cells Previously Exposed to Interleukin-1," Spine, vol. 27(12), pp. 1318-1325 (2002), Lippincott Williams & Wilkins Inc., U.S. Publication.
Chang, S.C. et al., "Cartilage-derived Morphogenetic Proteins—New Members of the Transforming Growth Factor-beta Superfamily Predominantly Expressed in Long Bones During Human Embryonic Development," The Journal of Biological Chemistry, vol. 269(45), 28227-28234 (1994), The American Society for Biochemistry and Molecular Biology Inc., U.S. Publication.
Nohe, A. et al., "Signal Trasduction of Bone Morphogenetic Protein Receptors," Cellular Signalling, vol. 16, 291-299 (2004), Elsevier, U.S. Publication.
Hatakeyama, Y. et al., "Smad Signaling in Mesenchymal and Chondroprogenitor Cells," The Journal of Bone and Joint Surgery—American Edition, vol. 85A Suppl. 3, pp. 13-18 (2003), The Journal of Bone and Joint Surgery Inc., U.S. Publication.
Li, Y. et al., "Transduction of Passaged Human Articular Chondrocytes with Adenoviral, Retroviral, and Lentiviral Vectors and the Effects of Enhanced Expression of SOX9," Tissue Engineering, vol. 10(3/4), pp. 575-584 (2004), Mary Ann Liebert Inc., U.S. Publication.
Aigner, T. et al., "SOX9 Expression Does Not Correlate With Type II Collagen Expression in Adult Articular Chondrocytes," Matrix Biology, vol. 22, pp. 363-372 (2003), Elsevier, U.S. Publication.
Paul, R. et al., "Potential Use of Sox9 Gene Therapy for Intervertebral Degenerative Disc Disease," Spine, vol. 28(8), pp. 755-763 (2003), Lippincott Williams & Wilkins Inc., U.S. Publication.
Sampath, T.K. et al., "In Vitro Transformation of Mesenchymal Cells Derived From Embryonic Muscle into Cartilage in Response to Extracellular Matrix Components of Bone," Proceedings of the National Academy of Sciences of the USA, vol. 81, pp. 3419-3423 (1984), National Academy of Sciences, U.S. Publication.
Israel, D.I. et al., "Heterodimeric Bone Morphogenetic Proteins Show Enhanced Activity In Vitro and In Vivo," Growth Factors, vol. 13, pp. 291-300 (1996), Taylor & Francis, Europe/U.S. Publication.
Heldin, C.H. et al., "TGF-beta Signalling From Cell Membrane to Nucleus Through SMAD Proteins," Nature, vol. 390, pp. 465-471 (1997), Macmillian Publishers Ltd., U.S. Publication.

(56) References Cited

OTHER PUBLICATIONS

Yamamoto, Y. et al., "Upregulation of the Viability of Nucleus Pulposus Cells by Bone Marrow-Derived Stromal Cells," Spine, vol. 29(14), pp. 1508-1514 (2004), Lippincott Williams & Wilkins Inc., U.S. Publication.
Hunter, C.J. et al., "The Functional Significance of Cell Clusters in the Notochordal Nucleus Pulposus—Survival and Signaling in the Canine Intervertebral Disc," Spine, vol. 29(10), pp. 1099-1104 (2004), Lippincott Williams & Wilkins Inc., U.S. Publication.
Kauppila, L.I., "Can Low-Back Pain Be Due to Lumbar-Artery Disease?," The Lancet, vol. 346 (8979), pp. 888-889 (1995), Elsevier, U.S. Publication.
Boggild, H., "Ischemia and Low Back Pain—Is It Time to Include Lumbar Angina as a Cardiovascular Disease?" Scandinavian Journal of Work, Environment & Health, vol. 32(1), pp. 20-21 (2006), Nordic Association of Occupational Safety and Health (NOROSH), Denmark/U.S. Publication.
Kauppila, L.I. et al, "Postmortem Angiographic Findings for Arteries Supplying the Lumbar Spine: Their Relationship to Low-Back Symptoms," Journal of Spinal Disorders, vol. 6(2), pp. 124-129 (1993), Raven Press Ltd., U.S. Publication.
Kurunlahti, M. et al, "Association of Atherosclerosis with Low Back Pain and the Degree of Disc Degeneration," Spine, vol. 24(20), pp. 2080-2084 (1999), Lippincott Williams & Wilkins Inc., U.S. Publication.
Cluroe, A.D. et al., "Combined Pathological and Radiological Study of the Effect of Atherosclerosis on the Ostia of Segmental Branches of the Abdominal Aorta," Pathology, vol. 24, pp. 140-145 (1992), Lippincott Williams & Wilkins Inc., U.S. Publication.
Kauppila, L.I. et al., "Lumbar Disc Degeneration and Atherosclerosis of the Abdominal Aorta," Spine, vol. 19(8), pp. 923-929 (1994), J.B. Lippincott Company, U.S. Publication.
Crock, H.V., "Chapter 2: Internal Disc Disruption," Practice of Spinal Surgery, Springer Vienna, pp. 35-92 (1983), U.S. Publication.
Kauppila, L.I., "Blood Supply of the Lower Thoracic and Lumbosacral Regions—Postmortem Aortagraphy in 38 Young Adults," Acta Radiologica, vol. 35(6), pp. 541-544 (1994), Informa Healthcare, Denmark/U.S. Publication.
Urban, J.P. et al., "Nutrition of the Intervertebral Disc," Spine, vol. 29(23), pp. 2700-2709 (2004), Lippincott Williams & Wilkins Inc., U.S. Publication.
Walker, M.N. et al., "Molecular Basis of Intervertebral Disc Degeneration," The Spine Journal, vol. 4, pp. 158S-166S (2004), Elsevier, U.S. Publication.
Mitchell, J.R. et al., "Aortic Size and Aortic Calcification: A Necropsy Study," Atherosclerosis, vol. 27, pp. 437-446 (1977), Elsevier/North-Holland Scientific Publishers Ltd., Europe/U.S. Publication.
Ross, R., "Cecil Textbook of Medicine,", vol. 1, 18th ed., p. 318-323 (1998), W.B. Saunders Company, Canada/U.S. Publication.
Naves, L.A. et al., "An Acid-Sensing Ion Channel that Detects Ischemic Pain," Brazilian Journal of Medicine & Biological Research, vol. 38(11), pp. 1561-1569 (2005), Assoção Brasileira de Divulgação Cientifica (ABDC), Brazil/U.S. Publication.
Iwabuchi, M. et al., "Effects of Anulus Fibrosus and Experimentally Degenerated Nucleus Pulposus on Nerve Root Conduction Velocity—Relevance of Previous Experimental Investigations Using Normal Nucleus Pulposus," Spine, vol. 26(15), pp. 1651-1655 (2001), Lippincott Williams & Wilkins Inc., U.S. Publication.
Ohshima, H. et al., "The Effect of Lactate and pH on Proteoglycan and Protein Synthesis Rates in the Intervertebral Disc," Spine, vol. 17(9), pp. 1079-1082 (1992), Lippincott-Raven Publishers, U.S. Publication.
Bibby, S.R. et al., "Effect of Nutrient Deprivation on the Viability of Intervertebral Disc Cells," Eur. Spine J., vol. 13, pp. 695-701 (2004), Springer-Verlag, U.S Publication.
Simons, M., "Angiogenesis: Where Do We Stand Now?" Circulation, vol. 111, pp. 1556-1566 (2005), American Heart Association, U.S. Publication.
Sharkey, A.M. et al., "Novel Antiangiogenic Agents for Use in Contraception," Contraception, vol. 71, pp. 263-271 (2005), Elsevier, U.S. Publication.
Dvorak, H.F., "Angiogenesis: Update 2005," Journal of Thrombrosis & Haemostasis, vol. 3, pp. 1835-1842 (2005), Blackwell Pub., Oxford, U.S. Publication.
Voros, G. et al., "Modulation of Angiogenesis During Adipose Tissue Development in Murine Models of Obesity," Endocrinology, vol. 146(10), pp. 4545-4554 (2005), The Endocrine Society, U.S. Publication.
Kroll, P. et al., "Which Treatment is Best for Which AMP Patient?" British Journal of Opthalmology., vol. 90, pp. 128-130 (2006), British Journal of Opthamology, Europe/U.S. Publication.
Folkman, J., "Role of Angiogenesis in Tumor Growth and Metastatis," Seminars in Oncology, vol. 29(Suppl. 16), pp. 15-18 (2002), Elsevier Science, U.S. Publication.
Maruotti, N. et al., "Angiogenesis in Rheumatoid Arthritis," Histology and Histopathology, vol. 21, pp. 557-566 (2006), Jimenez-Godoy, S.A. (Murcia, Spain), Europe/U.S. Publication.
Conway, E.M., "Angiogenesis: A Link to Thrombosis in Athero-Thrombotic Disease," Pathophysioly of Haemostasis and Thrombosis, vol. 33, pp. 241-248 (2003), S. Karger AG, Basel, Europe/U.S. Publication.
Mizukami, Y. et al., "Hypoxic Regulation of Vascular Endothelial Growth Factor Through the Induction of Phosphatidylinositol 3-Kinase/Rho/ROCK and c-Myc,"J. Biol. Chem., vol. 281(20), pp. 13957-13963 (2006), American Society for Biochemistry and Molecular Biology, Inc., U.S. Publication.
Liu, L. et al., "Regulation of Transcription and Translation by Hypoxia," Cancer Biology & Therapy, vol. 3(6), pp. 492-497 (2004), Landes Bioscience, U.S. Publication.
Ivan, M. et al., "HIF-alpha Targeted for VHL-Mediated Destruction by Proline Hydroxylation: Implications for O2 Sensing," Science, vol. 292, pp. 464-468 (2001), American Association for the Advancement of Science, U.S. Publication.
Gray, M.J. et al., "HIF-Alpha, STAT3, CBP/p300 and Ref-1/APE are Components of a Transcriptional Complex that Regulates Src-Dependent Hypoxia-Induced Expression of VGEF in Pancreatic and Prostate Carcinomas," Oncogene, vol. 24, pp. 3110-3120 (2005), Nature Publishing Group, U.S. Publication.
Li, J. et al., "Increased Responsiveness of Hypoxic Endothelial Cells to FGF2 is Mediated by HIF-1alpha-Dependent Regulation of Enzymes Involved in Synthesis of Heparin Sulfate FGF2-Binding Sites," Journal of Cell Science, vol. 115, pp. 1951-1959 (2002), The Company of Biologists Ltd., U.S. Publication.
Pear, W.S. et al., "Lasting Longer Without Oxygen: The Influence of Hypoxia on Notch Signaling," Cancer Cell, vol. 8, pp. 435-437 (2005), Elsevier, U.S. Publication.
Ceradini, D.J. et al., "Homing to Hypoxiz: HIF-1 as a Mediator of Progenitor Cell Recruitment to Injured Tissue," Trends Cardiovasc. Med., vol. 15(2), pp. 57-63 (2005), Elsevier, U.S. Publication.
Konttinen, Y.T. et al., "Transforming and Epidermal Growth Factors in Degenerated Intervertebral Discs," J. Bone Joint Surg. [Br], vol. 81-B, pp. 1058-1063 (1999), British Editorial Society of Bone and Joint Surgery, Europe/U.S. Publication.
Razaq, S. et al., "The Effect of Extracellular pH on Matrix Turnover by Cells of the Bovine Nucleus Pulposus," Eur. Spine J., vol. 12, pp. 341-349 (2003), Springer-Verlag, U.S. Publication.
Gruber, H.E. et al., "Immunolocalization of MMP-19 in the Human Intervertebral Disc: Implications for Disc Aging and Degeration," Biotech. Histochem., vol. 80(3-4), pp. 157-162 (2005), Taylor & Francis Group, U.S. Publication.
Seguin, C.A. et al., "Tumor Necrosis Factor-alpha Modulates Matrix Production and Catabolism in Nucleus Pupolsus Tissue," Spine, vol. 30(17), pp. 1940-1948 (2005), Lippincott Williams & Wilkins, Inc., U.S. Publication.
Omlor, G.W. et al., "Changes in Gene Expression and Protein Distribution at Different Stages of Mechanically Induced Disc Degeneration—An In Vivo Study on the New Zealand White Rabbit," J. Orthop. Res., vol. 24, pp. 385-392 (2006), Wiley Periodicals, Inc., U.S. Publication.

(56) References Cited

OTHER PUBLICATIONS

Haughton, V., "Imaging Intervertebral Disc Degeneration," J. Bone Joint Surg. Am., vol. 88-A(Supp. 2), pp. 15-20 (2006), The Journal of Bone and Joint Surgery, U.S. Publication.

Fingl, E. et al., "Goodman & Gillman's The Pharmacological Basis of Therapeutics, Chapter 1: General Principles," pp. 1-46 (1975, Fifth Edition), The McGraw Hill Companies, U.S. Publication.

Griffith, J.F. et al., "Vertebral Bone Mineral Density, Marrow Perfusion and Fat Content in Healthy Men and Men With Osteoporosis: Dynamic Contrast-Enhanced MR Imaging and MR Spectroscopy," Radiology, vol. 236(3), pp. 945-951 (2005), Radiological Society of North America, Inc., U.S. Publication.

Laroche, M. et al., "Comparison of the Bone Mineral Content of the Lower Limbs in Men With Ischaemic Atherosclerotic Disease," Clin. Rheumatol., vol. 13, pp. 611-614 (1994), Springer-Verlag, U.S. Publication.

Chen, Wei-Tsung et al., "Vertebral Bone Marrow Perfusion Evaluated With Dynamic Contrast-Enhanced MR Imaging: Significance of Aging and Sex," Radiology, vol. 220(1), p. 213-218 (2001), Radiological Society of North America, U.S. Publication.

Shih, T. et al., "Correlation of MR Lumbar Spine Bone Marrow Perfusion With Bone Mineral Density in Female Subjects," Radiology, vol. 233(1), pp. 121-128 (2004), Radiological Society of North America, U.S. Publication.

Soukane, M.D. et al., "Computation of Coupled Diffusion of Oxygen, Glucose and Lactic Acid in an Intervertebral Disc," Journal of Biomechanics, vol. 40, pp. 2645-2654 (2007), Elsevier, U.S. Publication.

Pfirrmann, C. et al., "Magnetic Resonance Classification of Lumbar Intervertebral Disc Degeneration," Spine, vol. 26(17), pp. 1873-1878 (2001), Lippincott Williams & Wilkins Inc., U.S. Publication.

Larsson, H.B.W. et al., "Myocardial Perfusion Modeling Using MRI," Magnetic Resonance Medicine, vol. 35, pp. 716-726 (1996), John Wiley & Sons, Inc., U.S. Publication.

Workie, D.W. et al., "Quantification of Dynamic Contrast-Enhanced MR Imaging of the Knee in Children With Juvenile Rheumatoid Arthritis Based on Pharmacokinetic Modeling," Magnetic Resonance Imaging, vol. 22, pp. 1201-1210 (2004). Elsevier, U.S. Publication.

* cited by examiner

A

B

A

B

A

B

THERAPEUTIC ANGIOGENESIS FOR TREATMENT OF THE SPINE

CROSS REFERENCE TO RELATED APPLICATIONS

This application claims priority under 35 U.S.C. §119 to U.S. Provisional Patent Application Nos. 60/920,254 (filed Mar. 27, 2007) and 61/022,266 (filed Jan. 18, 2008), each of which applications is expressly incorporated herein by reference in its entirety.

BACKGROUND OF THE INVENTION

1. Field of the Invention

Embodiments described herein pertain to the field of diagnosing and treating the spine, particularly lower back pain. Embodiments relate to methods for diagnosing and/or treating disorders causative, or being precursors to back pain. In particular embodiments relate to methods of increasing angiogenesis in specifically diagnosed conditions associated with back pain.

2. Related Art

Musculoskeletal disorders of the spine are an extremely common occurrence associated with debilitating back pain, leading to enormous psychosocial and economic ramifications. Lower-back pain is the leading source of disability in people under 45 years of age, and it results in significant economic losses (Frymoyer J W, et al. *The Adult Spine. Principles and Practice,* 143-150, 1997). Eighty percent of people in the United States will experience back pain at some point in their lifetime (Lively, M. W., *South Med J,* 95:642-646, 2002), and it is the second most common reason for symptomatic physician visits (Hart, L. G. et al. *Spine* 20:11-19, 1995). Causes of back pain range from injury, which presents as a minor problem, accelerating to a chronic disorder, as well as degenerative spine diseases that lead to degenerative spondylolisthesis and spinal stenosis. The vast majority of chronic back pain is associated with degeneration of the intervertebral disc, which can manifest in many different clinical conditions including spinal stenosis and instability, radiculopathy, myelopathy, and disc herniation. In order to attain proper understanding of spinal pain, particularly lower back pain, we will review some of the anatomy of the spine, particularly the lumbar area.

The human spine is composed of bony structures called vertebrae, separated by intervertebral discs. One of the main functions of the vertebrae is to provide structural support and protection for the spinal cord. Each vertebra includes a spinous process, a bony prominence behind the spinal cord, which shields the cord's nervous tissue on the back side, two bony protrusions on the sides called transverse processes, and a "body" in front of the spinal cord which provides a structural support for weight bearing. The average adult has 24 vertebrae, although at birth 33 are present. Reduction in the number of vertebrae is caused by fusion during normal development. The vertebrae are divided by anatomical locations with 7 in the neck, also called the cervical vertebrae, 12 in the middle back, called the thoracic vertebrae, 5 in the lower back, called the lumbar vertebrae, and the sacrum, which is actually formed from five fused vertebrae. The tailbone, called the coccyx is made of three fused vertebrae. Of these, the lumbar vertebrae are the largest, in part since they are responsible for carrying the majority of body weight. Consequently, the lumbar area is associated with the highest level of degeneration and is believed causative for a wide variety of pain-inducing syndromes.

Separating the vertebrae are soft intervertebral discs that, together with the two facet joints, allow for movement of the vertebrae and therefore provide the ability of the spine to move in various directions. The complex of two facet joints posteriorly and the disc anteriorly is referred to as a spinal segment. The intervertebral disc includes the annulus fibrosus, the nucleus pulposus, and the cartilage endplate. The nucleus pulposus includes anionic proteoglycans, such as aggrecan, that have high affinity for water, and provide a cushioning and shock-absorbing function. The annulus fibrosus encapsulates the nucleus pulposus, and is composed of concentrically organized layers of collagen fibrils (lamellae). The composition of the nucleus pulposus is distinctly different than the annulus fibrosus since the former primarily includes a jelly-like substance and high collagen type I, whereas the latter is made of a solid, fibrotic-like texture, primarily containing collagen type II. In an adult, the cartilage endplate is composed primarily of hyaline cartilage and serves to separate the nucleus pulposus and annulus fibrosus from the adjacent vertebral bone. Discogenic pain often arises from areas of the annulus fibrosus. As a matter of fact, pain-associated molecules such as Substance P and TNF (Tumor Necrosis Factor) have been identified in large concentrations in biopsy samples of patients suffering discogenic pain, but not in controls.

Each disc provides motion and binds the segments together through its 95% non-cellular and 5% cellular components. Nutrition to the disc cells (or chondrocytes) is provided by arteries that branch off of the major artery in the body (called the aorta) and wrap around each vertebral body, penetrating the bone along its circumference. The arteries course through the vertebral body (bone) and then turn towards the disc at either end. The oxygen, glucose and other nutrients are "dropped off" where the disc attaches to the bone and the capillaries and venules form a vascular loop. The cartilage that is in contact with these vascular loops is called the "endplate." The nutrients "diffuse" (or move through the endplate and disc tissue without being transported in blood vessels) into the middle of the disc (or nucleus). In addition to this pathway, arterioles deliver nutrients to the outer edge of the disc (annulus) directly (this pathway provides minimal nutrients to the nucleus in normal discs but might be exploited in angiogenic treatment). Once the nutrients reach the cell, they are taken up and utilized for the manufacture of the materials that make up the disc (extracellular matrix: collagen and proteoglycans). Recent studies have demonstrated that cartilage cells require oxygen to produce enough energy for the proper manufacture and maintenance of the extracellular matrix. If the cells do not receive enough oxygen, the manufacturing process diminishes and the disc becomes acidic (pH drops) (Horner, H et al. *Spine* 26:2543-2549, 2001). As the nutrient supply is cut off, the cells in the disc begin to die and the disc tissue begins to breakdown. This loss of nutrients is thought to be the initial cause of degenerative disc disease. As the disc continues to degenerate and the cell population decreases, the oxygen concentration may return to normal due to less demand. At this stage, regeneration still may be a possibility. However, excessive mechanical loading on a weakened structure precipitates further degeneration which may lead to structural defects such as endplate fracture, radial fissures and herniation. As cells continue to produce energy through anaerobic processes, low pH creates further cell death.

This nutrient supply can be blocked at various stages. The feeding arteries themselves can narrow due to atherosclerosis with resultant ischemia of the vertebral body. With less blood flowing through the vertebrae, less oxygen and nutrients are available to diffuse into the disc creating hypoxia, lower pH and cell death (Kauppila, L et al. *Spine* 22:1642-1649, 1997; Kurunlahit, M et al. *Radiology* 221:779-786, 2001). In addition to narrowing of the major lumbar vessels, many studies have demonstrated decreasing blood flow within the vertebral body as the reason for the loss of nutrients and degenerative disc disease. Degenerative disc disease due to nicotine and aging demonstrate a loss of nutritive blood vessels in the area supplying nutrients (Iwahahi, M et al. *Spine* 27:1396-1401, 2002; Boos, N et al. *Spine:* 27:2631-2644, 2002). Eventually, the endplate itself can become a hindrance to the diffusion of nutrients creating another obstacle to proper disc chondrocyte nutrition (Rajasekaran, S et al. *Spine* 29:2654-2667, 2004).

Although disc degeneration continues to have a tremendous and ever-increasing impact worldwide, current treatment options do not address the underlying cause. Current treatments include bed rest, nonsteroidal anti-inflammatory medication in the early phases of pathology, and procedures such as discectomy, arthroplasty (joint replacement), injection of artificial nucleus pulposus and fusion in the later phases when the prior approaches did not ameliorate pain. Such approaches are unpredictable, and deal almost exclusively with end-stage clinical manifestations, and therefore do nothing to alter the disease process itself. Additionally, procedures such as vertebral fusion result in the increased incidence of disc degeneration in the adjacent discs due to alterations in the biomechanical distribution of work-load.

Recent advances in both biotechnology and our understanding of the biochemical makeup and environment of the intervertebral disc have led to increased interest in the process of degeneration and the possibility of developing novel treatments aimed directly at disc preservation. Certain genes found to have significant impact on matrix synthesis and catabolism within the disc have provided targets for scientists seeking to alter the balance between the two. To this end, much attention over the past several years has centered on gene therapy, and these efforts have yielded some promising preclinical results with regard to its use in treating disc degeneration (Levicoff, E. A. et al. *Spine J* 5:287 S-296S, 2005). Unfortunately, none of these approaches are near clinical implementation at the time of this writing. Additionally, it is important to note that even in the circumstance that disc regeneration alone can be achieved through gene therapy or other interventional means, the underlying process that originally caused the degeneration must be addressed in order to prevent recurrence.

Currently, no biological treatment is widely available for disc degeneration. However, many different molecules of potential therapeutic benefit are being investigated. The focus of molecular therapy has been to prevent or reverse one or more aspects of these changes in the disc extracellular matrix. At least four different classes of molecules may be effective in disc repair. These include anticatabolics, mitogens, chondrogenic morphogens and intracellular regulators (Yoon, S. T. *Spine J* 5:280 S-286S, 2005; Masuda, K. et al. *Spine* 29:2757-2769, 2004; Shimer, A. L. et al. *Spine* 29:2770-2778, 2004). Hallmarks of disc degeneration include loss of proteoglycans, water, and Type II collagen in the disc matrix. Other changes in the matrix are less well defined, including loss of the higher molecular weight proteoglycans, collagen cross-linking and organization of the proteoglycan, etc. An important process in disc degeneration seems to be the change of the differentiated chondrocyte phenotype in the nucleus pulposus into a more fibrotic phenotype. Together these changes in the disc matrix lead to alterations of the disc and vertebral anatomy that ultimately are associated with a pathologic condition (Setton, L. A. et al. *Spine* 29:2710-2723, 2004; Roughley, P. J. *Spine* 29:2691-2699, 2004).

Due to the fact that matrix loss is a balance between matrix synthesis and degradation, it is possible to increase disc matrix by increasing synthesis or by decreasing degradation. One approach is to prevent matrix loss by inhibiting the degradative enzymes. Degenerated discs have elevated concentrations of matrix metalloproteinases (MMPs). Within the matrix, MMP activity is normally inhibited by tissue inhibitors of MMPs (TIMPs) (Roberts, S. et al. *Spine* 25:3005-3013, 2000; Nagase, H. et al. *J Biol Chem* 274:21491-21494, 1999; Wallach, C. J. et al. *Spine* 28:2331-2337, 2003). Wallach, et al. (*Spine* 28:2331-2337, 2003) tested whether one of these anticatabolic molecules, TIMP-1, could increase the accumulation of matrix proteoglycans with in vitro experiments. It was observed that TIMP-1 expression in disc cells increased accumulation and also increased the "measured synthesis rate" of proteoglycans (Wallach, et al. *Spine* 28:2331-2337, 2003). Chondrogenic morphogens are cytokines that not only possess mitogenic capability but are characterized by their ability to increase the chondrocyte-specific phenotype of the target cell. Most of the research in chondrogenic morphogens has been performed with transforming growth factor-β (TGF-β), bone morphogenetic proteins (BMPs) or growth and differentiation factors (GDFs). Chondrogenic morphogens are particularly attractive because they may reverse the fibrotic phenotype of disc cells to the more chondrocytic phenotype of disc nucleus cells in younger and more "normal" discs. By definition, these molecules are secreted molecules and hence can potentially act in autocrine, paracrine and endocrine fashion.

BMP-2 is another prototypic chondrogenic morphogen (Thompson, J. P. et al. *Spine* 16:253-260, 1991). Yoon, et al. (*Spine* 29:2603-2611, 2004) reported that recombinant human BMP-2 increased production of rat disc cell proteoglycans and significantly increased the chondrocytic phenotype of the disc cells as shown by increased aggrecan and Type II collagen gene expression, whereas there was no change in Type I collagen gene expression. Kim, et al. (*J Neurosurg* 99:291-297, 2003) reported that BMP-2 can partially reverse the inhibitory effect of nicotine on the synthesis of disc cell proteoglycan. BMP-7, also known as OP-1 (Osteogenic Protein-1), is another disc cell morphogen that has demonstrated potent in vitro activity in terms of enhancing matrix formation in disc cells (Masuda, K. et al. *J Orthop Res* 21:922-930, 2003; Zhang, Y. et al. *Am J Phys Med Rehabil* 85:515-521, 2004; Takegami, K. et al. *Spine* 27:1318-1325, 2002). Growth differentiation factor 5 (GDF-5) is also known as CDMP-1 (Cartilage-derived morphogenetic protein 1) and has also been considered for regeneration of disc cells. However, only in vitro experimentation has been performed to date (Chang, S. C. et al. *J Biol Chem* 269:28227-28234, 1994).

Intracellular regulators are a distinct class of molecules because they are not secreted and do not work through transmembrane receptors. These molecules are neither cytokines nor growth factors in the classical sense, and yet they can have effects that are quite similar to the secreted molecules discussed previously. This class of molecules typically controls one or more aspects of cellular differentiation. For instance, Sma-Mad (SMAD) proteins are intracellular molecules that mediate BMP-receptor signaling (Nohe, A. et al. *Cell Signal* 16:291-299, 2004; Hatakeyama, Y. et al. *J Bone Joint Surg Am* 85-A Suppl 3:13-18, 2003). Although there are no specific published papers on the effect of SMAD proteins on disc cells, proteins such as Smad-1 and Smad-5 are predicted to induce similar effects on disc cells as BMP-2, such as increasing proteoglycan and Type II collagen synthesis. Sox9 (transcription factor) is a chondrocyte marker that is a positive regulator of Type II collagen mRNA transcription (Yoon, S. T. *Spine J* 5:280 S-286S, 2005; Li, Y. et al. *Tissue Eng* 10:575-584, 2004; Aigner, T. et al. *Matrix Biol* 22:363-372, 2003). Paul, et al. (*Spine* 28:755-763, 2003) showed that Sox9 delivered by adenovirus can increase Sox9 expression and disc cell production of Type II collagen in in vitro experiments.

The success of a disc tissue engineering strategy is dependent on molecular cues to direct the differentiation of cells and affect their biosynthetic function. Many growth factors, including members of the transforming growth factor beta superfamily, affect the differentiation process of disc cells. This group of related proteins directs the induction of mesenchymal precursors to form mature skeletal tissues (Sampath, T. K. et al. *Proc Natl Acad Sci USA* 81:3419-3423, 1984). The activity of these molecules is complex and affects intercellular signaling pathways (Israel, D. I. et al. *Growth Factors* 13:291-300, 1996; Heldin, C. H. et al. *Nature* 390: 465-471, 1997). In addition, concentration and timing of presentation of the growth factor influences its activity. Depending on the tissue, the effects of a given morphogen may be different. For instance, the osteogenic molecule bone morphogenetic protein-7-osteogenic protein-1 (BMP-7/OP-1) has been shown to have a dramatic effect on disc cells, increasing their metabolic output of matrix proteins and rescuing them from the detrimental effects of Interleukin 1 (IL-1) (Takegami, K. et al. *Spine* 27:1318-1325, 2002). This data suggests that growth factors could play a useful role in a cell-based tissue engineering strategy.

Other yet to be identified factors direct cell-to-cell communication and appear to play an important role in the viability and metabolic activity of disc cells. Yamamoto, et al. (*Spine* 29:1508-1514, 2004) showed that cell proliferation and proteoglycan synthesis was significantly enhanced in disc cells cultured in a system that allowed direct cell-cell contact with bone marrow-derived stromal cells. In another study, Hunter, et al. (*Spine* 29:1099-1104, 2004) reported that enzymatic disruption of gap junctions produced a negative effect on cell viability, suggesting that communication among adjacent cells plays a vital role in cellular viability and function, and therefore interventions supporting their enhancement may be beneficial.

The invention relates to methods for diagnosing, treating or ameliorating painful conditions of the spine, particularly lower back pain. Embodiments are directed to classification of back pain that is based on specific parameters associated with ischemia, which is a decrease blood flow inflow due to arterial blockage, hypoperfusion, which is diminished microvascular blood flow, and the resulting hypoxia, which is decreased oxygen within the tissue, with resultant damage to tissue. Further embodiments relate to treatments for alleviating the state of ischemia, hypopersion and hypoxia in patients that may lead to therapeutic improvement.

SUMMARY OF THE INVENTION

In an embodiment, diagnosis of ischemic or hypoxic disc disease, often described as "lumbar ischemia," as a disorder is made by the two-part test of first excluding patients with a set of exclusion criteria, and further selecting patients having documented ischemia, hypoperfusion, and/or hypoxia, of the affected areas. Specific exclusion criteria include, for example, the presence of herniated disc, spinal infection, spinal tumor, spinal arthritis, and spinal canal stenosis.

Embodiments of the invention are directed to methods of diagnosing a condition responsible for degenerative disc disease or vertebral osteoporosis, which may include one or more of the following steps:
 a. assessing a patient by one or more of the following steps:
  i. classifying patency of said one or more lumbar segmental vessels;
  ii. determining blood perfusion in the anatomical areas supplied by said segmental vessels;
  iii. determining extent of disc degeneration or vertebral osteoporosis;
 b. correlating data collected from a(i) with data collected from a(ii) and with data collected from a(iii);
 c. producing an overall index of correlation; and
 d. comparing said index of correlation with an index of correlation generated from a healthy population.

In one embodiment, hypoxic and/or ischemic disc disease is treated by increasing perfusion in the affected area such as by injection of a composition that includes an angiogenic factor. In preferred embodiments, injection is around the vertebrae or directly into the vertebral body. In other embodiments, a localized delivery system capable of forming a gel-like structure may be used to deliver the angiogenic factor. Preferably, the delivery system includes components of extracellular matrix that provide conditions suitable for angiogenesis. In other embodiments, the extracellular matrix components may be hyaluronic acid fragments. In other embodiments, the extracellular matrix components may be derivatives of collagen, or perlecan. Preferably, the gel-like structure includes a polymer capable of slow release such as a poloxamer block copolymer (Pluronic®, BASF), basement membrane preparation (Matrigel®, BD Biosciences) or collagen-based matrix such as described in U.S. Pat. No. 6,346,515, which is incorporated herein by reference in its entirety.

In another embodiment, hypoxic and/or ischemic disc disease is treated by administration of a medical device that generates a continuous release of a composition that includes an angiogenic factor into tissue and/or circulation so as to promote neoangiogenesis, and specifically, collateralization in the area(s) proximal to hypoperfusion. In some embodiments, the composition further includes stem cells. The medical device may include a slow release pump such as an implantable indwelling or osmotic pump or a localized delivery system such as a polymer capable of slow release as described above.

In another embodiment, the composition delivered by the medical device includes both a therapeutically sufficient concentration of a growth factor that stimulates angiogenesis and a chemotactic agent. Some growth factors, such as fibroblast growth factor 1 (FGF-1), are themselves chemotactic. The chemotactic agent recruits cells capable of causing or promoting angiogenesis. In some embodiments, a chemotactic agent such as stromal cell-derived factor 1 (SDF-1) is included in the composition with the growth factor.

Assessment of perfusion followed by therapy that increases the rate of perfusion, followed by a subsequent assessment of perfusion so as to identify the ideal conditions for stimulation of perfusion on an individualized basis.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings:

FIG. 3 shows a normal MRA scan with normal discs. Pixilation of perfusion data and a bar for comparison are shown. The white at the top of the bar is maximum $K^{trans}$. The side arrow indicates that the perfusion data shows relatively high flow of blood through vertebrae;

DETAILED DESCRIPTION OF THE INVENTION

Figure 1:
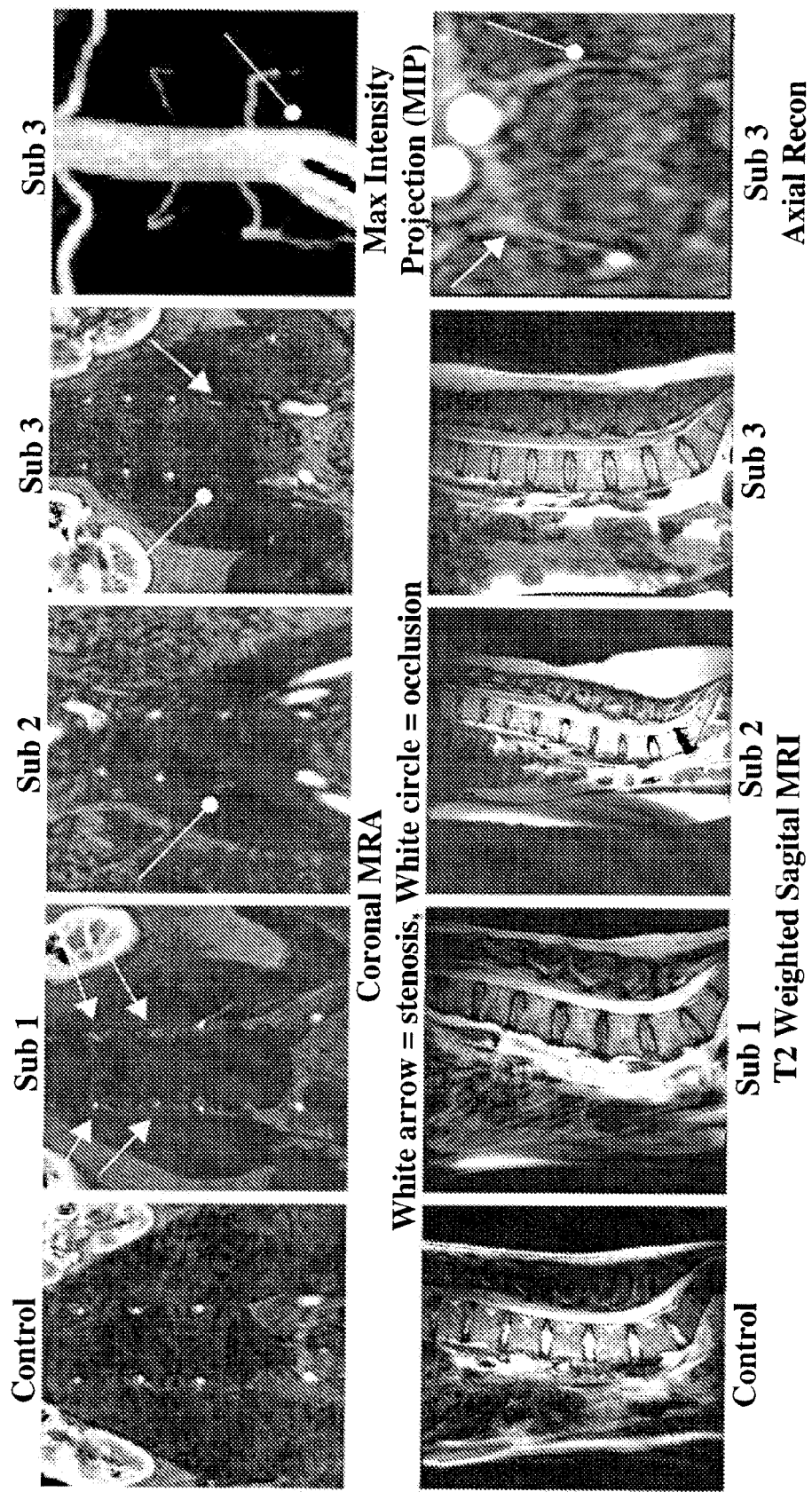
FIG. 1 represents coronal MRA (magnetic resonance angiography) and T2 weighted sagittal MRI (magnetic resonance imaging) for a healthy control subject compared to 3 subjects (Sub1, Sub2, Sub3) with symptoms of chronic lower back pain and degenerative disc disease (DDD). Also shown is a Max Intensity Projection (MIP) and Axial reconstruction for Sub3. The control is a 20-year old subject with normal discs and segmental vessels from L1 to L5. The arrows indicate areas of stenosis or occlusion. Sub1 shows areas of stenosis indicated by the arrows. Sub2 shows areas of occlusion indicated by the arrow. Sub3 shows areas of both occlusion (left arrow) and stenosis (right arrow)

Although some embodiments are described below, these are merely representative and one of skill in the art will be able to extrapolate numerous other applications and deviates that are still within the scope of the invention disclosed.

Numerous studies suggested the notion that the vast majority of patients with long-term back pain, intractable by conventional approaches, have occluded lumbar/middle sacral arteries and that occlusion of these arteries is associated with disc degeneration (Kauppila, L. I. et al. *Spine* 29:2147-2152, 2004). However, none of these studies proposed treatment methodologies, or placed it in the context of disease-specific diagnosis. These studies have included observations that patients with high LDL (low density lipoprotein) cholesterol complained of more severe back symptoms than those with normal value (Kauppila, L. I. et al. *Spine* 29:2147-2152, 2004). These findings support previous studies that occlusion of lumbar/middle sacral arteries is associated with lower back pain and disc degeneration (Kauppila, L. I. *Lancet* 346:888-889, 1995; Boggild, H. *Scand J Work Environ Health* 32:20-21, 2006; Kauppila, L. I. et al. *J Spinal Disord* 6:124-129, 1993; Kauppila, L. I. et al. *Spine* 22:1642-1647, 1997; Kurunlahti, M. et al. *Spine* 24:2080-2084, 1999) and that occlusion of these arteries may be due to atherosclerosis (Cluroe, A. D. et al. *Pathology* 24:140-145, 1992; Kauppila, L. I. et al. *Spine* 19:923-929, 1994). Epidemiologic and post-mortem studies indicate that atheromatous lesions in the abdominal aorta may be related to disc degeneration and long-term back symptoms (Kauppila, L. I. *Lancet* 346:888-889, 1995; Boggild, H. *Scand J Work Environ Health* 32:20-21, 2006; Kauppila, L. I. et al. *J Spinal Disord* 6:124-129, 1993; Kauppila, L. I. et al. *Spine* 22:1642-1647, 1997; Kurunlahti, M. et al. *Spine* 24:2080-2084, 1999)). However, these studies have not provided a means for classification of patients, or for therapeutic interventions. Additionally, since disc degeneration is not necessarily a painful process, the relevance of occluded spinal arteries remains enigmatic.

Embodiments described herein provide hypoxic and/or ischemic disc disease as a defined disease subset, in which patients may be specifically classified that are amenable to treatment with means capable of stimulating perfusion. Specifically, in one embodiment, hypoxic and/or ischemic disc disease is diagnosed as stenosis or the complete occlusion of one or more blood vessels associated with the lumbar area. The importance of perfusion is seen in the following discussion regarding lumbar vasculature. It is known that the blood supply of the lumbar spine is derived from the aorta through the lumbar and middle sacral arteries. The upper four segments of the lumbar spine receive their blood supply from the four pairs of the lumbar arteries, which arise in the posterior wall of the abdominal aorta. The fifth lumbar segment is supplied partly by the middle sacral artery (arising in the bifurcation) and partly by branches of the iliolumbar arteries (arising from the internal iliac arteries) (Crock, H. V. The Practice of Spinal Surgery, Springer-Verlag, 1983); Kauppila, L. I. *Acta Radiol* 35:541-544, 1994). Nutrition of the avascular intervertebral disc occurs by diffusion through the vertebral endplates from the blood vessels in the vertebral bodies above and below the disc (Urban, J. P. et al. *Spine* 29:2700-2709, 2004; Walker, M. H. et al. *Spine J* 24:158 S-166S, 2004). Cholesterol plaques in the wall of the aorta obliterate orifices of lumbar and middle sacral arteries and decrease blood supply of the lumbar spine and its surrounding structures. As a result, structures with precarious nutrient supply, such as the intervertebral discs, gradually degenerate (Cluroe, A. D. et al. *Pathology* 24:140-145, 1992; Mitchell, J. R. et al. *Atherosclerosis* 27:437-446, 1977; Ross, R. *Cecil's Textbook of Medicine* 318-23, 13, 1988). Reduced blood flow causes hypoxia and tissue dysfunction. It also hampers removal of waste products, such as lactic acid. These changes are found by the current invention to mean that in some patients irritation of nociceptive nerve endings occurs, causing pain, as well as lead to deterioration and atrophy of the structures involved (Naves, L. A. et al. *Braz J Med Biol Res* 38:1561-1569, 2005; Iwabuchi, M. et al. *Spine* 26:1651-1655, 2001; Ohshima, H. et al. *Spine* 17:1079-1082, 1992; Bibby, S. R. et al. *Eur Spine J* 13:695-701, 2004). Accordingly, the invention provides both a method of quantifying and relating hypoperfusion with pathological and symptomatic features and also methods of selecting patients that would benefit from interventions aimed at stimulating perfusion in the area of the spine, or areas associated with not only lack of blood supply but also removal of metabolic wastes.

In one embodiment of the invention, a patient is diagnosed with hypoxic and/or ischemic disc disease and is treated by increasing localized perfusion through the use of angiogenesis induction. The process of new blood vessel formation (angiogenesis) can occur naturally, or be induced through three various means, namely: vasculogenesis, arteriogenesis, and angiogenesis. For the purpose of this invention, all three will be referred to as "angiogenesis." Angiogenesis is associated with de novo capillary formation from post-capillary venules, is hypoxia-driven, and is associated with a 2-3 fold increase in blood flow. Arteriogenesis is the remodeling of pre-existing vascular channels (collaterals) or de novo artery formation. It is stimulated by local changes in perfusion (shear stress), as well as cellular influx, and associated with a 20-30 fold increase in blood flow. Vasculogenesis is responsible for embryonic vascular development and includes de novo formation of vascular channels initiated by circulating vascular precursor cells. Furthermore, it is considered to be ischemia and injury initiated (Simons, M. *Circulation* 111: 1556-1566, 2005). The term "angiogenesis" is used in this application to encompass all three technical terms due to the functional uncertainty at present regarding the continuum of biological and physiological differences among these subdivisions.

Angiogenesis is known to occur physiologically during implantation/embryogenesis (Sharkey, A. M. et al. *Contraception* 71:263-271, 2005), wound healing (Dvorak, H. F. *J Thromb Haemost* 3:1835-1842, 2005), and expansion of adipose mass (Voros, G. et al. *Endocrinology* 146:4545-4554, 2005). Pathologically, uncontrolled angiogenesis is associated with a variety of diseases such as macular degeneration (Kroll, P. et al. *Br J Opthalmol* 90:128-130, 2006), cancer (Folkman, J. *Semin Oncol* 29:15-18, 2002), arthritis (Maruotti, N. et al. *Histol Histopathol* 21:557-566, 2006), and atherosclerosis (Conway, E. M. *Pathophysiol Haemost Thromb* 33:241-248, 2003). One common aspect of adult angiogenesis is the issue of tissue hypoxia. In all situations of tissue expansion, cells are dependent on the microvasculature for nutrients and oxygen supply, as well as removal of metabolic waste products. Accordingly during tissue growth, cells begin to "sense" a lack of oxygen. This triggers a cascade of events that culminates in angiogenesis. During pathological conditions, such as the conditions associated with hypoxic and/or ischemic disc disease, the lack of oxygen is induced through hypoperfusion. The hypoperfusion may occur due to, for example, atherosclerosis. In some pathological conditions, the normal angiogenic response to hypoxia is absent or substantially diminished.

Although numerous methods of physiological stimulation of angiogenesis under hypoxia are known and thereby useful for the practice of the current invention (Mizukami, Y. et al. *J Biol Chem* 2006), one of the most well characterized pathways involves activation of the Hypoxia Inducible Factor-1 (HIF-1), transcription factor (Liu, L. et al. *Cancer Biol Ther* 3:492-497, 2004). This protein is only functionally active as a heterodimer of HIF-1α and HIF-1β, which are both basic helix-loop-helix proteins. While the latter is known to be relatively stable, the former has a half-life of less than 5 minutes under physiological conditions due to rapid proteasomal degradation by the oxygen sensitive von Hippel-Lindau (VHL) E3-ubiquitin ligase system (Ivan, M. et al. *Science* 292:464-468, 2001). When cells experience hypoxia, HIF-1α half-life is increased since the degradation by VHL E3-ubiquitin ligase is dependent on proline hydroxylation, which requires molecular oxygen. Therefore, this protein modification plays a key role in mammalian oxygen sensing. Activation of this transcription factor leads to gene expression of numerous angiogenesis related genes such as VEGFs (Gray, M. J. et al. *Oncogene* 24:3110-3120, 2005), FGF-2 response genes (Li, J. et al. *J Cell Sci* 115:1951-1959, 2002), notch signaling (Pear, W. S. et al. *Cancer Cell* 8:435-437, 2005), and up regulation of stromal derived factor (SDF-1), which chemoattracts endothelial precursors during angiogenesis (Ceradini, D. J. et al. *Trends Cardiovasc Med* 15:57-63, 2005). There are numerous variations by which angiogenesis can occur; however, the basic steps involve remodeling of the extracellular matrix through matrix metalloproteases (MMPs), chemoattraction of either precursor endothelial cells or existing endothelial cells from an adjacent vessel, proliferation of the endothelial cells, tube formation and stabilization. Embodiments relate to transfection of genes encoding HIF-1 into areas of lumbar hypoperfusion in order to induce normalization of perfusion, or in some cases hyperperfusion in order to ameliorate or significantly treat hypoxic and/or ischemic disc disease. Embodiments described herein relate to, among other things, utilization of molecules that either induce the expression of HIF-1, or conversely delay the degradation of HIF-1 or components thereof including but not limited to FGFs.

In one embodiment of the invention, the stimulation of perfusion in the area proximal to the pain generator is performed by providing proper nutrition so as to enhance healing and production of appropriate proteins in said disc. It is known that the synthesis of proteoglycans in the nucleus pulposus occurs naturally by the cellular component of the nucleus pulposus. Specific growth factors such as transforming growth factor-β (TGF-β) and epidermal growth factor (EGF) are involved in the stimulation of proteoglycan synthesis. Interestingly, in patients with degenerative disc disease, the amount of these cytokines is reduced in comparison to healthy nucleus pulposus cells (Konttinen, Y. T. et al. *J Bone Joint Surg Br* 81:1058-1063, 1999). This reduction may be due to decreased nutrient supply and cellular viability within said nucleus. Another reason for inhibition of proteoglycan synthesis is lower pH caused by ischemia and/or hypoperfusion of the lumbar area (Razaq, S. et al. *Eur Spine J* 12:341-349, 2003). The low pH also appears to be involved in another process associated with discogenic pain, said process comprising up regulation of matrix metalloproteases expression. It is known that matrix metalloproteases are involved in cleaving proteoglycans, and that up regulation of matrix metalloprotease activity is associated with disc degeneration (Gruber, H. E. et al. *Biotech Histochem* 80:157-162, 2005). Activation of matrix metalloproteases is known to be induced by inflammatory cytokines such as TNF and IL-1 (Seguin, C. A. et al. *Spine* 30:1940-1948, 2005). Additionally, animal studies have demonstrated that hyperphysiological loading of the disc segment induces up regulation of matrix metalloproteases (OmLor, G. W. et al. *J Orthop Res* 24:385-392, 2006), but have not assessed the influence of perfusion. Accordingly, in one embodiment of the invention, the increase of localized perfusion is used to augment proteoglycan content in said nucleus pulposus, as well as to lead to suppression, in some instances, of MMP activation.

In one embodiment, patients with advanced lumbar back pain are screened to determine whether the pain is associated with disc degeneration. This screening is a common medical practice and includes techniques such as physical examination, radiographic studies, MRI and bone scan to diagnose "discogenic" pain, or pain associated with degeneration of the annulus fibrosus, nerve irritation by the nucleus pulposus, or other chronic pain. Patients with rheumatoid arthritis, spinal infections or tumors, acute nerve compression and arthritis are excluded from eligibility for treatment using the methods and compositions described in the present invention. In a variety of cases, patients treated with the invention disclosed will be refractory to conventional treatments such as anti-inflammatory medication or analgesics. In a more specific embodiment, patients are diagnosed based on degeneration of a single or plurality of discs using magnetic resonance imaging. In preferred embodiments, disc degeneration can be estimated from regular lumbar T1 and T2-weighted MR sagittal fast spin-echo (FSE) and T2-weighted FSE axial images. Preferably, the intervertebral discs may be classified according to three grades: grade 0, discs with high signal intensity or only slightly blurred intranuclear cleft, which represent normal discs; grade 1, discs with decreased signal intensity but normal height, which represent mild degeneration; and grade 2, discs with markedly decreased signal intensity and height loss, which represent severe degeneration. In preferred embodiments, the signal intensities of intervertebral discs are compared with those of cerebrospinal fluid. In some embodiments, specific grades of disc degeneration are chosen for treatment. In a particularly preferred embodiment, parameters used for MR imaging of discs includes: TR 3200 ms, TE 119 ms milliseconds, and thickness of 4.0 mm with gap 0.4 mm.

Numerous methods are known to identify the disc segment causative of lower back pain, as well as areas of hypoperfusion. These include diffusion-weighted imaging, magnetic resonance imaging, diffusion tensor imaging, magnetic resonance spectroscopy, functional magnetic resonance imaging, dynamic computed tomography and magnetic resonance imaging, T2 relaxometry MRI, CT-scan (computed tomography scan), and provocative discography (Haughton, V. *J Bone Joint Surg Am* 88 Suppl 2:15-20, 2006). Any of these techniques may be used alone or in combination to diagnose lumbar ischemia as described.

In one embodiment, the area of hypoperfusion is identified using technetium-99m Sestamibi in conjunction with single photon emission computed tomography (SPECT) imaging. This radiolabelled lipophilic cation is injected intravenously at concentrations ranging from 200-1790 MBq, more preferably 500-1000 MBq, and even more preferable at approximately 750 MBq. Imaging is performed with a gamma camera and absorption/perfusion is quantified using various software packages known to one skilled in the art. In some embodiments, to attain appropriate images of the lumbar area, the camera is rotated 360 degrees.

In other embodiments, various other methodologies for detecting hypoperfusion are employed, for example, PET-CT (positron emission tomography—computed tomography), MR diffusion angiography, and, for example, fluorescent peptide-based methodologies.

Once an area of hypoperfusion is identified, and a patient is diagnosed with hypoxic and/or ischemic disc disease, induction of neovascularization is performed so as to enhance localized perfusion to the area of need. In one embodiment, genes are introduced from exogenous sources so as to promote angiogenesis. It is known that genes may be introduced by a wide range of approaches including adenoviral, adeno-associated, retroviral, alpha-viral, lentiviral, Kunjin virus, or HSV vectors, liposomal, nano-particle mediated as well as electroporation and Sleeping Beauty transposons. Genes with angiogenic stimulatory function that may be transfected include, but are not limited to: VEGFs, FGF-1, FGF-2, FGF-4, and HGF. Additionally, transcription factors that are associated with up regulating expression of angiogenic cascades may also be transfected into cells used for treatment of lower back pain. The genes include: HIF-1α, HIF-2, NET (norepinephrine transporter gene), and NF-kB (nuclear factor-kappa B). Antisense oligonucleotides, ribozymes or short interfering RNA (ribonucleic acid) may be transfected into cells for use for treatment of lower back pain in order to block expression of antiangiogenic proteins such as IP-10 (Interferon-gamma-inducible 10 kD protein).

Selection of genes or techniques for introduction of said genes in vivo may be performed in vitro prior to administration so as to allow for methods of screening and selecting the combination that is most angiogenically potent. Testing may be performed by various methodologies known to one skilled in the art. In terms of assessing angiogenic potential, these methodologies include, but are not limited to:

A. Angiogenic activity may by assessed by the ability to stimulate endothelial cell proliferation in vitro using human umbilical vein endothelial cells (HUVECs) or other endothelial cell populations. Assessment of proliferation may be performed using tritiated thymidine incorporation or by visually counting the proliferating endothelial cells. A viability dye such as MTT or other commercially available indicators may be used;

B. Angiogenic activity may also be assessed by the ability to support cord formation in subcutaneously implanted matrices. The matrices, which may include Matrigel® or fibrin gel, are loaded with cells that do not have intrinsic angiogenic potential, for example fibroblasts, transfecting said cells with said genes, and implanting said cells subcutaneously in an animal. The animal may be an immunodeficient mouse such as a SCID (severe combined immunodeficiency) or nude mouse in order to negate immunological differences. Subsequent to implantation, formation of endothelial cords generated from endogenous host cells may be assessed visually by microscopy. In order to distinguish cells stimulating angiogenesis versus host cells responding to the cells stimulating angiogenesis, a species-specific marker may be used;

C. Angiogenic activity may be assessed by the ability to accelerate angiogenesis occurring in the embryonic chicken chorioallantoic membrane assay. Cells transfected with angiogenic genes may be implanted directly, or via a matrix, into the chicken chorioallantoic membrane on embryonic day 9 and cultured for a period of approximately 2 days. Visualization of angiogenesis may be performed using in vivo microscopy; and D. Angiogenic activity may be assessed by the ability to stimulate neovascularization in the hind limb ischemia animal model. In one embodiment, patients diagnosed with hypoxic and/or ischemic disc disease are treated using gene therapy in a localized manner.

In one embodiment, patients diagnosed with hypoxic and/or ischemic disc disease are treated using gene therapy in a localized manner. Specifically, the gene for FGF-1 is administered in a composition of nucleic acid sequences or one or more triplex DNA compounds, and a nonionic block copolymer. The gene administered is under control of a strong promoter, for example, the CMV (cytomegalovirus) promoter. The nonionic block copolymer may be CRL-8131 as described in U.S. Pat. No. 6,933,286 (which is incorporated herein by reference in its entirety). Specifically, 300 milligrams of CRL-8131 may be added to 10 mL of 0.9% NaCl and the mixture is solubilized by storage at temperatures of 2-4° C. until a clear solution is formed. An appropriate amount of a FGF-1 expressing plasmid diluted in PBS (phosphate buffered saline) is added to the mixture and micelles associating the copolymer and the compound are formed by raising the temperature above ° C. and allowing the suspension of micelles to equilibrate. The equilibrated suspension is suitable for administration.

In other embodiments, it may be desirable to utilize an angiogenesis-stimulating protein for administration in a therapeutically effective amount. The protein may be selected from proteins known to stimulate angiogenesis including, but not limited to: TPO (thyroid peroxidase), SCF (stem cell factor), IL-1 (interleukin 1), IL-3, IL-6, IL-7, IL-8, IL-11, flt-3L (fms-like tyrosine kinase 3 ligand), G-CSF (granulocyte-colony stimulating factor), GM-CSF (granulocyte monocyte-colony stimulating factor), Epo (erythropoietin), FGF-1, FGF-2, FGF-4, FGF-5, FGF-20, IGF (insulin-like growth factor), EGF (epidermal growth factor), NGF (nerve growth factor), LIF (leukemia inhibitory factor), PDGF (platelet-derived growth factor), BMPs (bone morphogenetic protein), activin-A, VEGF (vascular endothelial growth factor), VEGF-B, VEGF-C, VEGF-D, P1GF, angiopoietins, ephrins, and HGF (hepatocyte growth factor). In some preferred embodiments, administration of the angiogenesis-stimulating protein is performed by injection directly into a vertebral body. In some embodiments, the angiogenic-stimulating protein is co-administered with stem or progenitor cells. The stem cells may be embryonic stem cells or adult stem cells.

As used herein, the terms "treating," "treatment," "therapeutic," or "therapy" do not necessarily mean total cure or abolition of the disease or condition. Any alleviation of any undesired signs or symptoms of a disease or condition, to any extent, can be considered treatment and/or therapy. In addition, asymptomatic degenerative disc disease may be the focus of treatment utilizing angiogenesis. Furthermore, treatment may include acts that may worsen the patient's overall feeling of well-being or appearance.

The term "therapeutically effective amount" is used to indicate an amount of an active compound, or pharmaceutical agent, that elicits the biological or medicinal response indicated. This response may occur in a tissue, system, animal or human and includes alleviation of the symptoms of the disease being treated.

The exact formulation, route of administration and dosage for the composition and pharmaceutical compositions disclosed herein can be chosen by the individual physician in view of the patient's condition. (See, e.g., Fingl et al. 1975, in "The Pharmacological Basis of Therapeutics", Chapter 1, which is hereby incorporated herein by reference in its entirety). The dosage may be a single one or a series of two or more given in the course of one or more days, as is needed by the patient. Where no human dosage is established, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. Alternatively, the compositions disclosed herein may be administered by continuous infusion, preferably at a dose of each active ingredient up to approximately 400 ug per day. Thus, the total daily dosage by parenteral administration will typically be in the range of approximately 0.1 to approximately 400 ug. In some embodiments, the compounds will be administered for a period of continuous therapy, for example for a week or more, or for months.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC (high-performance liquid chromatography) assays or bioassays can be used to determine plasma concentrations.

Dosage intervals can also be determined using MEC value. Compositions should be administered using a regimen which maintains plasma levels above the MEC for approximately 10% and approximately 90% of the time, preferably between approximately 30% and approximately 90%, and most preferably between approximately 50% and approximately 90%.

The amount of composition administered will, of course, be dependent on the subject being treated, on the subject's weight, the severity of the affliction, the manner of administration and the judgment of the prescribing physician.

In some embodiments a carrier solution is desired. The carrier solutions may be selected based on properties such as viscosity, ease of administration, ability to bind solution over a period of time, and general affinity for the agent delivered. The solutions may be modified or additives incorporated for modification of biological properties. Starting solutions may include certain delivery polymers known to one who is skilled in the art. These could be selected from, for example: polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, polyethylene oxide, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acryl substituted cellulose acetates, non-degradable polyurethanes, polystyrenes, polyvinyl fluoride, polyvinyl imidazole, chlorosulphonated polyolefin, and polyvinyl alcohol.

Administration may be performed under fluoroscopy or other means in order to allow for localization in proximity of the cause of hypoperfusion. Acceptable carriers, excipients, or stabilizers are also contemplated within the current invention; said carriers, excipients and stabilizers being relatively nontoxic to recipients at the dosages and concentrations employed, and may include buffers such as phosphate, citrate, and other organic acids; antioxidants including ascorbic acid, n-acetylcysteine, alpha tocopherol, and methionine; preservatives such as hexamethonium chloride; octadecyldimethylbenzyl ammonium chloride; benzalkonium chloride; phenol, benzyl alcohol, or butyl; alkyl parabens such as methyl or propyl paraben; catechol; resorcinol; cyclohexinol; 3-pentanol; and mecresol; low molecular weight polypeptides; proteins, such as gelatin, or non-specific immunoglobulins; amino acids such as glycine, glutamine, asparagine, histidine, arginine, or lysine; monosaccharides, disaccharides, and other carbohydrates including glucose, mannose, or dextrins; chelating agents such as EDTA (ethylenediaminetetraacetic acid); sugars such as sucrose, mannitol, trehalose, or sorbitol; salt-forming counter-ions such as sodium.

In an embodiment, a localized medical device is implanted using an attachment means onto an anatomical structure that resides proximal to the blood vessel supplying the area of hypoperfusion. In another embodiment, the attachment is performed using an anchoring means; said anchoring means attaching said medical device to the vertebral bone proximal to one of the lumbar or medial sacral arteries. The medical device includes the functionality of time-course release of an angiogenic factor. The medical device may be composed of a solid casing with internal gel-like fluid containing desired angiogenic factor. The gel-like fluid may be a cryoprecipitate, an administration matrix, or a composition of various polymers suitable for the sustained release of said angiogenesis promoting factor.

In another embodiment, treatment of hypoxic and/or ischemic disc disease includes the use of a biodegradable implant. The biodegradable implant contains a biodegradable delivery means, or carrier, as well as angiogenic factors; said angiogenic factors are capable of stimulating sufficient neovascularization to overcome local hypoxia. One preferred angiogenic factor is fibroblast growth factor 1 (FGF-1). However, other recombinant naturally derived, in vitro derived, and in vivo derived angiogenic factors may also be used. In some embodiments, the biodegradable implant which contains said angiogenic factors contains a carrier. The carrier is preferably chosen so as to remain within the implanted site for a prolonged period and slowly release the angiogenic factors contained therein to the surrounding environment. This mode of delivery allows said angiogenic factors to remain in therapeutically effective amounts within the site for a prolonged period. By providing said angiogenic factors within a carrier, the advantage of releasing said angiogenic factors directly into the target area is realized. In some embodiments, the implant's carrier is provided in an injectable form. Injectability allows the carrier to be delivered in a minimally invasive and preferably percutaneous method. In some embodiments, the injectable carrier is a gel. In others, the injectable carrier includes hyaluronic acid (HA).

In some embodiments, the carrier of the graft includes a porous matrix having an average pore size of at least approximately 25 micrometers. Preferably, the porous matrix has an average pore size of between approximately 25 micrometers and approximately 110 micrometers. When the average pore size is in this range, it is believed that that porous matrix will also act as a scaffold for in-migrating cells capable of becoming cells stimulatory of angiogenesis in the targeted area. Numerous examples of organic materials that can be used to form the porous matrix are known to one of skill in the art; these include, but are not limited to, collagen, polyamino acids, or gelatin.

The collagen source may be artificial (i.e., recombinant), or autologous, or allogenic, or xenogeneic relative to the mammal receiving the implant. The collagen may also be in the form of an atelopeptide or telopeptide collagen. Additionally, collagens from sources associated with high levels of angiogenesis, such as placentally derived collagen, may be used. Examples of synthetic polymers that can be used to form the matrix include, but are not limited to, polylactic acids, polyglycolic acids, or combinations of polylactic/polyglycolic acids. Resorbable polymers, as well as non-resorbable polymers, may constitute the matrix material. One of skill in the art will appreciate that the terms porous or semi-porous refer to the varying density of the pores in the matrix.

Scaffold structures may be used in some embodiments of the invention for anchoring or substantially causing adhesion between the implant and anatomical structures; the anatomical structures may be bone, cartilage, nerve, tendon, and ligament. In some embodiments, the method of adhering the implant to the anatomical structures may be a gel. The gel, together with the implant, can be injected to the graft site, in some embodiments under arthroscopic fluid conditions. The gel can be a biological or synthetic gel formed from a bioresorbable or bioabsorbable material that has the ability to resorb in a timely fashion in the body environment.

Suitable scaffold agents are also known to one of skill in the art, and may include hyaluronic acid, collagen gel, alginate gel, gelatin-resorcin-formalin adhesive, mussel-based adhesive, dihydroxyphenylalanine-based adhesive, chitosan, transglutaminase, poly(amino acid)-based adhesive, cellulose-based adhesive, polysaccharide-based adhesive, synthetic acrylate-based adhesives, platelet rich plasma (PRP) gel, platelet poor plasma (PPP) gel, clot of PRP, clot of PPP, Matrigel®, Monostearoyl Glycerol co-Succinate. (MGSA), Monostearoyl Glycerol co-Succinate/polyethylene glycol (MGSA/PEG) copolymers, laminin, elastin, proteoglycans, poly(N-isopropylacrylamide), poly(oxyalkylene), a copolymer of poly(ethylene oxide)-poly(propylene oxide), polyvinyl alcohol and combinations thereof.

In some embodiments, a pliable scaffold is preferred so as to allow the scaffold to adjust to the dimensions of the target site of implantation. For instance, the scaffold can include a gel-like material or an adhesive material, as well as a foam or mesh structure. Preferably, the scaffold can be a bioresorbable or bioabsorbable material. The scaffold can be formed from a polymeric foam component having pores with an open cell pore structure. The pore size can vary, but preferably, the pores are sized to allow tissue or angiogenic ingrowth. In some embodiments, the pore size is in the range of approximately 40 to approximately 900 micrometers. The polymeric foam component can, optionally, include a reinforcing component, such as, for example, woven, knitted, warped knitted (i.e., lace-like), non-woven, and braided structures. In some embodiments where the polymeric foam component includes a reinforcing component, the foam component can be integrated with the reinforcing component such that the pores of the foam component penetrate the mesh of the reinforcing component and interlock with the reinforcing component. In some embodiments, the angiogenic growth factors are predominantly released from a sustained delivery device by its diffusion through the sustained delivery device (preferably, through a polymer). In others, the angiogenic factors are predominantly released from the sustained delivery device by the biodegradation of the sustained delivery device (preferably, biodegradation of a polymer). In some embodiments, the implant includes a bioresorbable material whose gradual erosion causes the gradual release of the angiogenic factors. In some embodiments, the implant includes a bioresorbable polymer. Preferably, the bioresorbable polymer has a half-life of at least one month. Accordingly, in some embodiments, the implant includes the co-polymer poly-DL-lactide-co-glycolide (PLG) admixed with the angiogenic factors.

In some embodiments, the implant essentially includes a hydrogel. Hydrogels can also be used to deliver said angiogenic factors in a time-release manner to the area of hypoperfusion. A "hydrogel," as defined herein, is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep said angiogenic factors in proximity to either the blood vessel causative of hypoperfusion, or the area associated with hypoperfusion. In some embodiments, said hydrogel is a fine, powdery synthetic hydrogel. Suitable hydrogels exhibit an optimal combination of such properties as compatibility with the matrix polymer of choice, and biocompatibility. The hydrogel can include one or more of the following: polysaccharides, proteins, polyphosphazenes, poly(oxyethylene)-poly(oxypropylene) block polymers, poly(oxyethylene)-poly(oxypropylene)block polymers of ethylene diamine, poly(acrylic acids), poly(methacrylic acids), copolymers of acrylic acid and methacrylic acid, polyvinyl acetate, and sulfonated polymers.

In another embodiment of the invention, a direct injection of an angiogenic factor into the ischemic vertebral body can be performed to produce angiogenesis within the vertebral body (and therefore the subchondral capillary bed that supplies the disc with its nutrients). The vertebral pedicle, a route used in pedicle screw spinal implants as well as vertebroplasty and kyphoplasty treatments of vertebral compression fractures, can easily be entered with a direct catheter for injection. The pedicle communicates with the vertebral body. The injection can be done percutaneously or with open surgery. This injection can be short term (one injection) or be delivered within an indwelling catheter for longer administration. In addition, a device could be introduced through the pedicle that can be placed within the vertebral body for long term introduction of factor(s). In addition to the vertebral pedicle, direct placement into the vertebral body through the vertebral body cortical wall could be a method of delivering angiogenic factors to the vertebrae. This is performed at the time of open surgery or via the percutaneous route.

Embodiments of the invention are directed to detection of ischemia-associated osteoporosis and subsequent treatment through angiogenic stimulation. While previous studies have demonstrated an association between atherosclerosis and osteoporosis, a causal relationship was not identified. The invention discloses a novel diagnostic algorithm that can be utilized in the diagnosis and selection of patients for subsequent treatment utilizing pro-angiogenic approaches. To date, a diagnostic imaging algorithm has not been developed since no vascular basis for spinal disease has been accepted in the field of spinal medicine and surgery. In one aspect of the invention, magnetic resonance angiography (MRA), a special type of MR which creates three-dimensional reconstructions of vessels containing flowing blood, is utilized to identify vascular abnormalities. By imaging the segmental arteries, a rating system is developed measuring the amount of patency of the vessels. The following system is an example of such a system:

Arterial Occlusion (L1-L5):2 vessels (left and right)
0=both vessels are patent
1=one vessel is stenotic
2=both vessels are stenotic
3=one vessel is occluded
4=one vessel is occluded and one stenotic
5=both vessels are occluded In some embodiments of the invention, diffusion studies (Diffusion Weighted images or DWI) are performed for analyzing the diffusion characteristics of the disc and correlating it with disc degeneration and segmental artery stenosis.

In other embodiments, perfusion studies are performed using methods such as Dynamic Contrast Enhanced MR Imaging for analysis of Perfusion of the vertebral bodies. Finally, combinations of imaging strategies are also disclosed in the current invention for generation of algorithms to include/exclude patients for the treatment of lower back pain, and/or vertebral osteoporosis.

Diffusion Studies

Diffusion Weighted Images (DWIs) have mostly been used in the spine to help delineate benign and malignant vertebral collapse fractures (Griffith, J. F. et al. *Radiology* 236(3): 945-951, 2005). However, the technique appears to be well suited for research in analyzing the diffusion characteristics of the normal disc and correlating it with disc degeneration (Rajasekaran, S. et al. *Spine* 29(23):2664-2667, 2004) and segmental artery stenosis and/or vertebral body perfusion abnormalities. Solute transfer into the central portion of the disc (nucleus) is dependent upon the concentration of the solute at the vertebral endplate (correlated with vascular perfusion) and the diffusion characteristics of the disc. Abnormalities in diffusion contribute to disc degeneration. Analyzing diffusion properties among various patient populations (as well as normal controls) may lead to data that can contribute to the ischemic disc disease diagnosis.

Perfusion Studies

Dynamic Contrast Enhanced MR Imaging for analysis of Perfusion of the vertebral bodies has been described using a 1.5 Tesla scanner in the evaluation of the possible ischemia-related osteoporosis (Laroche, M. et al. *Clin Rheumatol* 13:611-614, 1994; Chen, Wei-Tsung et al. *Radiology* 220(1): 213 2001; Shih, T. et al. *Radiology* 233(1):121-128, 2004). However, the correct imaging parameters on a 3 Tesla scanner have not been previously developed. The present inventors have determined imaging parameters for a 3 Tesla scanner. The images were acquired with a Philips Achieva 3T system. For all imaging protocols, these were used: 330 mm*300 mm FOV and a 6-element SENSE torso RF coil. The imaging session started with the perfusion scan following the standard calibration scans. A 3D FFE sequence with TR/TE=3.5 ms/1.5 ms, SENSE factor: 2.5(AP), 2(RL), flip angle=30°, with dynamic scan time of 2.9 seconds was used and 7 slices in sagittal orientation with 6 mm thickness and 1.9 mm*1.9 mm pixel size were acquired. A total of 114 volumes were collected, 2 of them before contrast injection. After the dynamic scans, T1 weighted anatomical images in sagittal plane were collected using a TSE sequence with 0.5*0.5*3 mm$^3$ voxel size. 14 slices cover the same volume as dynamic scans. TR/TE=900 ms/10 ms, flip angle=90°. This was followed by a T2 weighted scan that had identical geometry to T1 scans and TR/TE=2940 ms/120 ms, flip angle=90°. Finally, contrast-enhanced angiography scans were collected. Contrast bolus arrival was observed real-time using a single, 50 mm thick coronal slice using FFE sequence in dynamic mode, collecting images every 0.5 seconds. Once the contrast arrived in the descending aorta, actual 3D angiography scan was started by the operator immediately. TR/TE=5.1 ms/1.78 ms, voxel size=0.8*0.8*1.5 mm$^3$, with SENSE factor=4 was used to acquire 50 coronal slices. Segmental vessels on MRA were graded as occluded, stenotic or open. Discs were graded as per Pfirrmann (6). ROI-averaged time course (from whole vertebra and/or end-plate) was converted into a fractional enhancement time course and analyzed using a compartmental model (Larsson, et al., *MRM*, 1996, 35: 716-26; Workie, et al., *MRI*, 2004, 1201-10). The model fitting results in 6 parameters: $K^{trans}$ (apparent volume transfer constant), $k_{ep}$ (rate constant), Vp' (apparent fractional plasma volume), E (extraction fraction), tlag (arrival time of tracer in the ROI) and baseline.

Data were collected from control and experimental subjects to ascertain an "ischemic index" of the vertebral bodies. This is applied to future research on ischemic/hypoxic disc disease. These data are correlated with the degree of disc degeneration and the degree of segmental artery stenosis to define a new clinical entity and the proper imaging tools for diagnosis of spinal, particularly lumbar, ischemia. Since perfusion measures the amount of blood supply coursing through the vertebral bodies and therefore the amount of nutrition available for the disc, this value may be important in developing treatment schemes based on improving the blood supply to the vertebrae (and therefore, the disc). In addition, since the ROI (region of interest) can be placed anywhere on the scanned spine, the spinal cord can be investigated with this technique, providing another category of spinal disease (spinal cord injury) with vascular anatomy imaging (MRA) and simultaneous Dynamic Perfusion.

Spinal MR Spectroscopy

A loss of perfusion at the vertebral endplate results in less oxygen available for diffusion across into the nucleus of the disc. Since simple diffusion is the mechanism for solute transport within the disc and not a pumping action (Soukane, M. D. et al. *Journal of Biomechanics* 40:2645-2654, 2007), the oxygen concentration at the vertebral endplate is critical. Loss of oxygen (hypoxia) results in the chondrocytes shifting to anaerobic metabolism to produce energy. This inefficient process is associated with a shutdown in matrix production and resulting poor matrix repair and maintenance (Horner, H et al. *Spine* 26: 2543-2549, 2001). High field strength spectroscopy (at least 3 Tesla) may be extremely important in the delineation of metabolic abnormalities associated with ischemia within the intervertebral disc. It has been demonstrated that lactate levels are elevated in discs dependent upon anaerobic metabolism. Therefore, lactate could be used as a biochemical marker signifying a disc that is "stressed" and at risk. In addition, low pH (associated with high lactate) has been demonstrated to be a biochemical mediator of discogenic pain. Other useful markers that may correlate with ischemia/hypoxia and the painful, degenerative disc include, but are not limited to, determination of 31 P levels as an indicator of energy level, water content as an indicator of proteoglycan content and disc size. A larger disc indicates less efficient distribution of oxygen and an increase in anaerobic metabolism.

Combination Imaging Strategies

Combining Imaging studies may provide important insight into the description of heretofore unknown vascular diseases of the spine. In addition, combining vertebral perfusion (of the vertebrae above and below the disc studied) with segmental artery stenosis and the degree of degenerative disc disease (and possibly diffusion and spectroscopy data) may describe a "new" etiology for subsets of patients with degenerative disc disease and osteoporosis.

Either in combination or separate, growth factors, synthetic or treated allograft or xenograft tissue for scaffold (or extra-cellular matrix) and stem cells may be utilized to "engineer" disc tissue with the goal of regenerating living tissue within the intervertebral disc. If the degenerative disc to be treated requires that ischemia or hypoxia related causes need to be diagnosed and treated first or in combination with the tissue engineering techniques, then the diagnosis is ischemic disc disease.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted, to limit the scope of the invention.

EXAMPLES

Example 1

Lumbar Segmental Artery Analysis Combined with Vertebral Body Dynamic Perfusion

The vertebral arterial tree and vertebral body blood flow were simultaneously evaluated for the purpose of vascular mapping of the lumbar spine. The goal of this study was (1) to develop a safe and reproducible technique of MRA and perfusion utilizing one injection of contrast, (2) to measure vertebral perfusion and compare intra-subject and inter-subject results with the degree of segmental artery stenosis and degenerative disc disease, and (3) to begin evaluating normal controls.

Both the lumbar MRA and dynamic perfusion portions were contrast enhanced. Subjects were volunteers with degenerative disc disease (DDD) and low back pain and were referred from spine surgeon practices or by word of mouth. The images were acquired with a Philips Achieva 3T system. For all imaging protocols, we used 330 mm*300 mm FOV and a 6-element SENSE torso RF coil. The imaging session started with the perfusion scan following the standard calibration scans. A 3D FFE sequence with TR/TE=3.5 ms/1.5 ms, SENSE factor: 2.5(AP), 2(RL), flip angle=30°, with dynamic scan time of 2.9 seconds was used and 7 slices in sagittal orientation with 6 mm thickness and 1.9 mm*1.9 mm pixel size were acquired. A total of 114 volumes were collected, 2 of them before contrast injection. After the dynamic scans, T1 weighted anatomical images in sagittal plane were collected using a TSE sequence with 0.5*0.5*3 mm$^3$ voxel size. Fourteen slices covered the same volume as dynamic scans. TR/TE=900 ms/10 ms, flip angle=90°. This was followed by a T2 weighted scan that had identical geometry to T1 scans and TR/TE=2940 ms/120 ms, flip angle=90°. Finally, contrast enhanced angiography scans were collected. Contrast bolus arrival was observed real-time using a single, 50 mm thick coronal slice using FFE sequence in dynamic mode, collecting images every 0.5 seconds. Once the contrast arrived in descending aorta, actual 3D angiography scan was started by the operator immediately. TR/TE=5.1 ms/1.78 ms, voxel size=0.8*0.8*1.5 mm$^3$, with SENSE factor=4 was used to acquire 50 coronal slices.

Segmental vessels on MRA were graded as occluded, stenotic or open. Discs were graded as per Pfirrmann (Pfirrmann, C. et al, *Spine* 26:1873-1878, 2001). Region of interest (ROI)-averaged time course (from whole vertebra and/or end-plate) was converted into a fractional enhancement time course and analyzed using a compartmental model (Larsson, et. al. *MRM* 35:716-726, 1996; Workie, et. al. *MRI*, 1201-1210, 2004). The model fitting resulted in 6 parameters: $K^{trans}$, (apparent volume transfer constant), $k_{ep}$ (rate constant), Vp' (apparent fractional plasma volume), E (extraction fraction), tlag (arrival time of tracer in the ROI) and baseline.

FIG. 1 shows Coronal MRA for a healthy control subject compared to 3 subjects with symptoms of chronic lower back pain and DDD (Sub1, Sub2, Sub3). The control was a 20-year old with normal discs and segmental vessels from L1 to L5. The markers indicate areas of stenosis or occlusion. Sub1 showed areas of stenosis indicated by the arrows. Sub2 showed areas of occlusion indicated by the circle. Sub3 showed areas of both occlusion (left circle) and stenosis (right arrow).

Each of the three symptomatic subjects demonstrated at least one segmental vessel that was either occluded or stenotic. Subjects 1 and 3 demonstrated decreased $K_{trans}$ at the level of the vascular lesion(s) with subject 3 demonstrating an order of magnitude lower value at all vertebral levels indicating a perfusion abnormality beyond the MRA identified lesions (FIG. 1). The other perfusion parameters ($k_{ep}$, Vp and E) can be extracted from the acquired data and are helpful in the interpretation. Pixel by pixel images can be generated of any parameter (and through any slice) for visual comparison.

Figure 2:
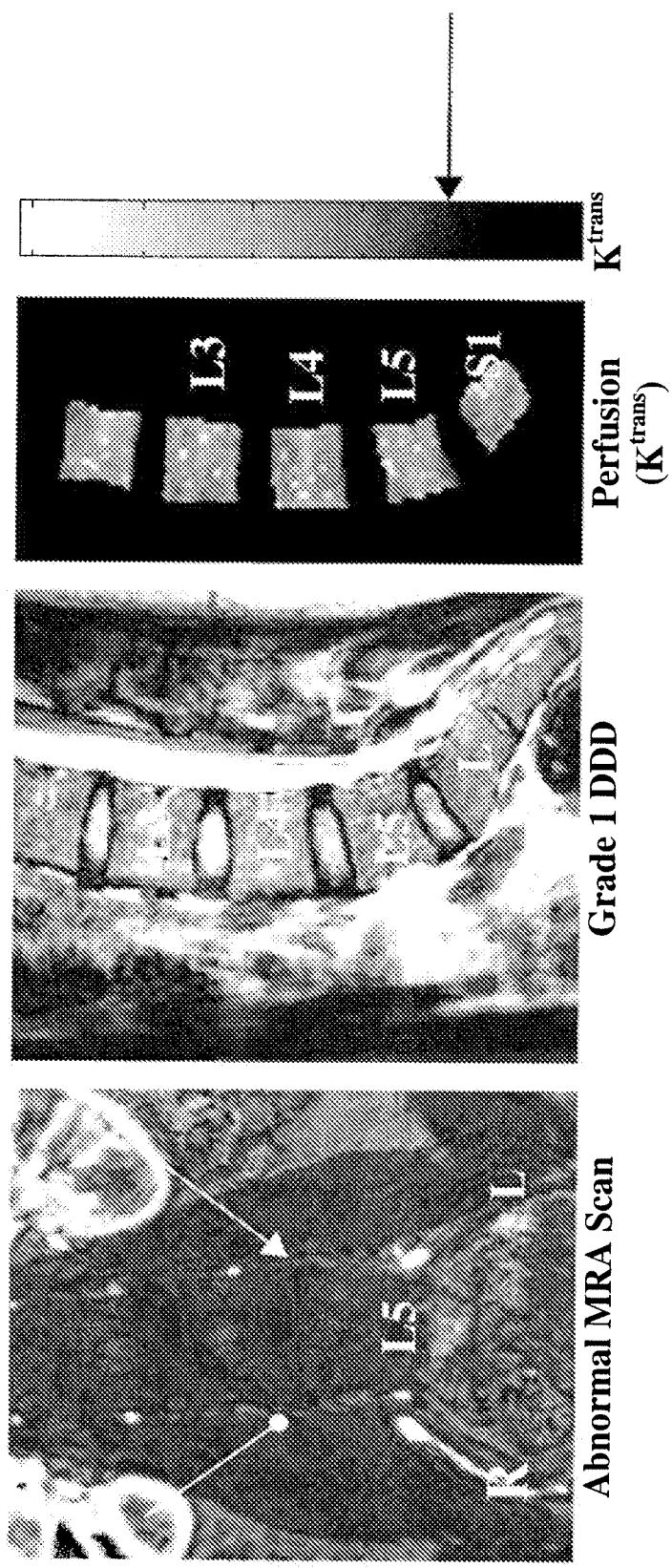
FIG. 2 shows data for subject 3 (sub3) of FIG. 1. The abnormal MRA scan shows areas of both occlusion (left—white circle) and stenosis (right—white arrow). Pixilation of perfusion data and a bar for comparison are shown. The white at the top of the bar is maximum $K^{trans}$. The side arrow indicates that the perfusion data shows relatively low flow of blood through vertebrae.
Figure 3:
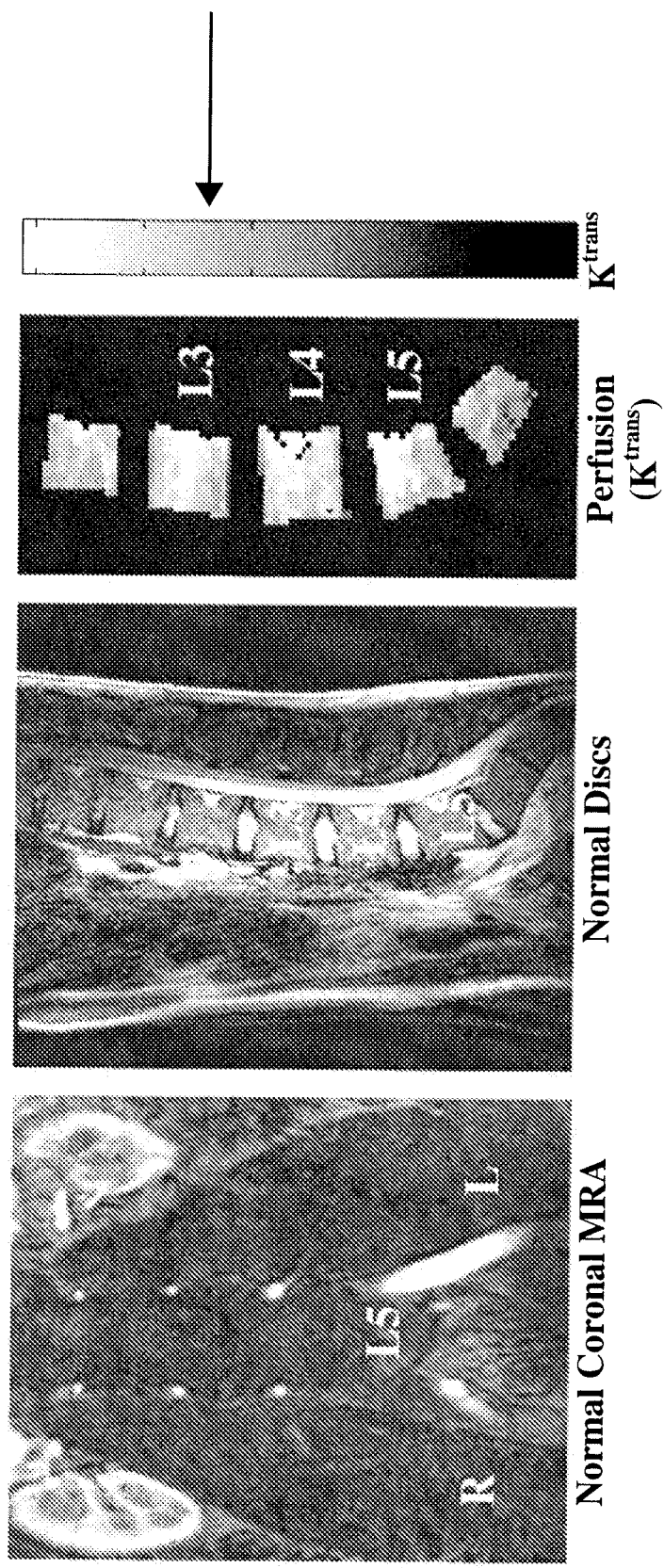
FIG. 3 shows data for the control of FIG. 1.

FIG. 2 shows the data for subject 3. Consistent with FIG. 1, the left arrow in Abnormal MRA Scan shows a stenotic left L4 segmental vessel. The right circle shows an occluded right L4 segmental vessel. The perfusion ($K^{trans}$) shows sub3 has low blood flow through the vertebrae compared to the control subject shown in FIG. 3 where normal (higher) blood flow through the vertebrae is shown by the position of the side arrow. Scans can be color coded with the color map demonstrating the disease visually and is more adaptable for clinical use. Using this technique, data can be entered into a pooled multicenter database. Subsets of patients that may have a significant vascular and resultant ischemic/hypoxic component to their disease can then be identified and studied.

TABLE 1

$K^{trans}$ values of L3-S1 vertebral bodies for 3 subjects

| Vertebrae | Control | Sub 1 | Sub 2 | Sub 3 |
|---|---|---|---|---|
| L3 | .215 | .146 | .160 | .090 |
| L4 | .220 | .148 | .156 | .084 |
| L5 | .205 | .170 | .160 | .075 |
| S1 | .149 | .160 | .146 | .053 |
| | | $K^{trans}$ | | |

Table 1 shows $K^{trans}$ values at sacral (S1) and Lumbar (L3, L4, and L5) positions for the healthy control and three symptomatic subjects (sub1-3). Decreased $K^{trans}$ values are observed in all symptomatic subject vertebral levels. $K^{trans}$ for sub3 is approximately 2-3 fold lower at each vertebra compared to sub1 and sub2.

Figure 4:
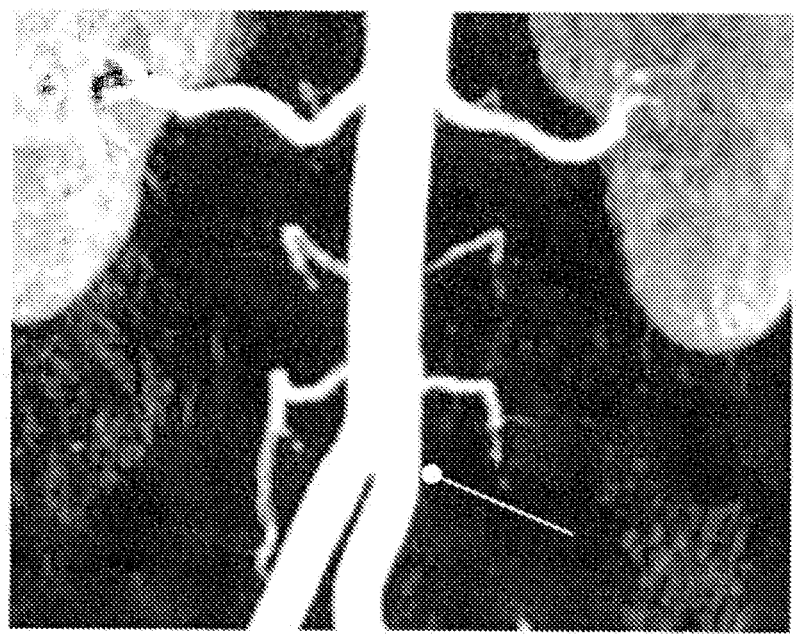
FIG. 4 shows a Max Intensity projection (MIP) (A) and Axial reconstruction (B) for sub3. The circle in FIG. 4A and the right-side circle in FIG. 4B point to an occluded vessel. The left hand arrow in FIG. 4B points to a stenosis.
Figure 4:
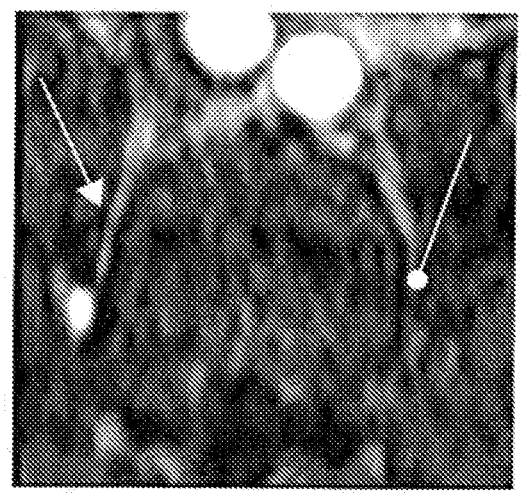

FIG. 4 shows a Max Intensity projection (MIP) (A) and Axial reconstruction (B) for sub3. The circle in FIG. 4A and the right-side circle in FIG. 4B point to an occluded vessel. The left hand arrow in FIG. 4B points to a stenosis.

A method for studying the vascular anatomy and dynamics of the spine in one scanning session using a contrast agent is demonstrated. Spinal anatomy, vascular anatomy and sophisticated perfusion data can be obtained. $K^{trans}$ is the rate of transfer of contrast delivered to the interstitial tissue, while the $k_{ep}$ is the rate the delivered contrast is cleared from the interstitial tissue, or "wash out". In addition, E (the extraction fraction of contrast during its initial passage within a given volume [ROI]) is another helpful parameter. If decreased blood supply is an etiologic factor in a subset of patients with DDD, this technique provides a mechanism by which investigators can study this disease in vivo.

Figure 5:
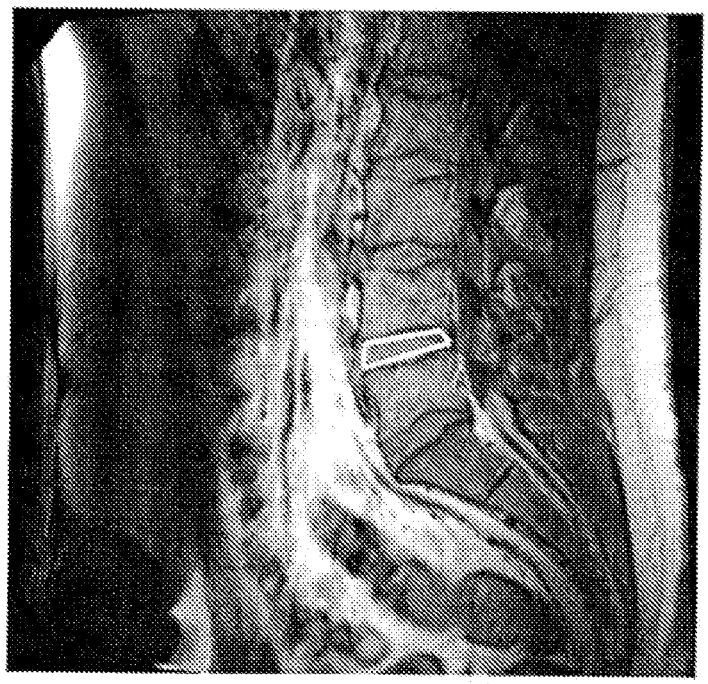
FIG. 5A shows MR (magnetic resonance) spectroscopy of the L4-5 disc and FIG. 5B shows MR spectroscopy of the L5-1 disc.
Figure 5:
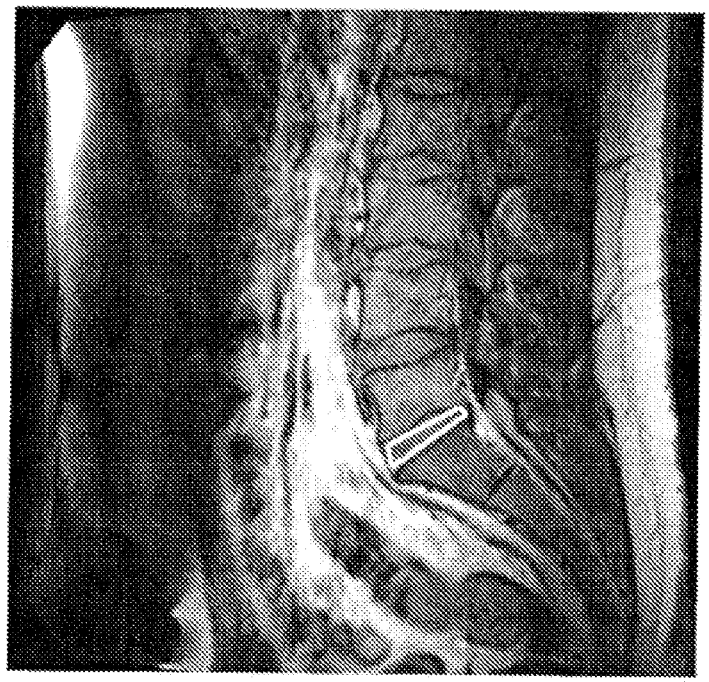
Figure 6:
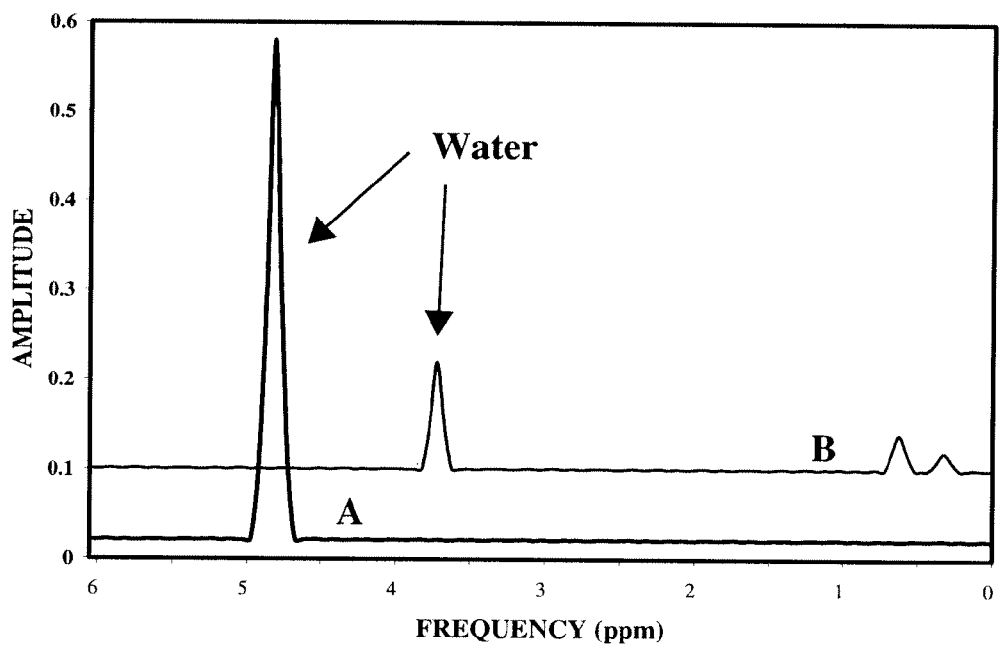
FIG. 6A shows the water-unsuppressed spectra of FIG. 5A and FIG. 5B.
FIG. 6B shows the same spectrum as FIG. 6A but with water suppressed. "Lip"=lipid. "Lac"=lactate.
Figure 6:
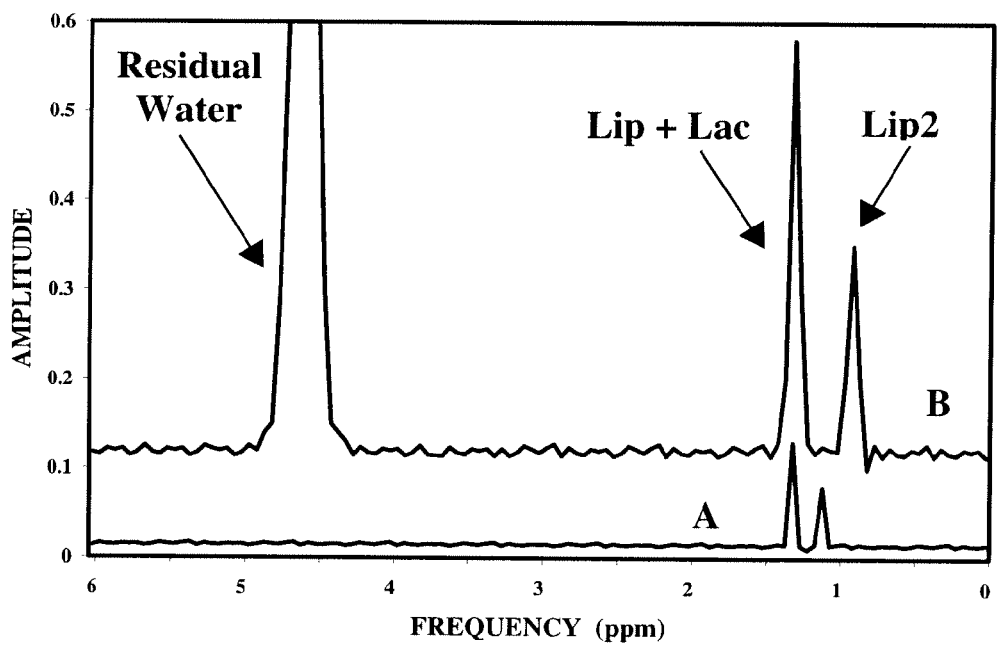

Newer MR techniques such as MR Spectroscopy can be added to identify metabolic abnormalities within the disc. For example, lactate, an end product of anaerobic metabolism, may be increased in the disc that obtains its nutrients from vertebral bodies with poor perfusion. FIG. 5 demonstrates 2 discs that have undergone spectroscopy. FIG. 5A shows the L4-5 disc (Disc A) and FIG. 5B shows the L5-1 disc (Disc B). When water is suppressed (FIG. 6B), Disc B has a higher lipid+lactate peak [(Lip+Lac)/water=0.405] compared to Disc A [(Lip+Lac)/water=0.019], indicating a higher lactate concentration. This higher lactate may be associated with anaerobic metabolism and discogenic pain.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A method of diagnosing a patient with back pain as having an ischemic disc disease comprising:
    a. selecting a patient with back pain;
    b. obtaining image data of at least a portion of a spine of the patient, the image data including at least a portion of an intravertebral vasculature proximal to an intervertebral disc endplate;
    c. quantifying localized perfusion of at least the portion of the intravertebral vasculature proximal to the intervertebral disc endplate from the image data; and
    d. diagnosing said patient as having the ischemic disc disease where the quantified localized perfusion indicates hypoperfusion within the at least a portion of the intravertebral vasculature proximal to the intervertebral disc endplate.

2. The method of claim 1, wherein said step of quantifying localized perfusion comprises measuring an amount of patency of at least the portion of the intravertebral vasculature proximal to the intervertebral disc endplate.

3. The method of claim 2, wherein said step of quantifying localized perfusion comprises measuring local changes in extracellular fluid pH.

4. The method of claim 1, wherein the step of obtaining image data of at least athe portion of the spine of the patient comprises obtaining image data of at least the portion of the spine of the patient using a magnetic resonance imaging (MR) system.

5. The method of claim 1, wherein said step of quantifying localized perfusion comprises quantifying localized perfusion proximate to both a superior and an inferior endplate of an intervertebral disc.

6. The method of claim 1, wherein the step of obtaining image data of at least the portion of the spine of the patient comprises obtaining image data of at least the portion of the spine of the patient using a dynamic contrast enhanced magnetic resonance imaging (DCE-MR) system.

7. The method of claim 6, wherein the step of obtaining image data of at least the portion of the spine of the patient using the dynamic contrast enhanced magnetic resonance imaging system includes the use of a contrast agent comprising an exogenous MR observable contrast agent.

8. The method of claim 1, wherein said step of quantifying localized perfusion comprises determining a reduction in blood flow by comparison to blood vessels of individuals that do not suffer from back pain associated with hypoperfusion.

9. The method of claim 1, wherein the step of quantifying localized perfusion of at least the portion of the intravertebral vasculature proximal to the intervertebral disc endplate comprises measuring the blood flow of at least a portion of the intravertebral vasculature proximal to the intervertebral disc endplate.

10. The method of claim 1, wherein said step of obtaining image data comprises obtaining image data using an imaging system selected from a group consisting of MR Sagittal fast spin-echo (FSE), magnetic resonance spectroscopy, dynamic computed tomography, computed tomography (CT), provocative discography, single photon emission computed tomography (SPECT), and any combination thereof.

11. The method of claim 1, wherein the image data comprises one or more two-dimensional (2D) images.

12. The method of claim 1, wherein the image data comprises one or more three-dimensional (3D) images.

13. A method of treating a patient with back pain having an ischemic disc disease comprising:
    a. diagnosing at least one patient as having an ischemic disc disease by performing the method of claim 1; and
    b. treating the patient having ischemic disc disease by increasing the localized perfusion of at least a portion of the intravertebral vasculature.

14. The method of claim 13, wherein the step of increasing the localized perfusion of at least the portion of the intravertebral vasculature comprises augmenting blood flow by inducing angiogenesis.

15. The method of claim 13, wherein said step of increasing the localized perfusion of at least the portion of the intravertebral vasculature comprises administering a growth factor.

16. The method of claim 15, wherein said growth factor is selected from the group consisting of FGF-1 through FGF-23.

17. The method of claim 13, wherein said step of increasing the localized perfusion of at least the portion of the intravertebral vasculature comprises administering at least one angiogenic factor by injection into or around a vertebral body.

18. The method of claim 13, further comprising a step of regenerating living tissue of an intervertebral disc.

19. The method of claim 18, wherein said step of regenerating living tissue comprises regenerating living tissue by using at least one item selected from the group consisting of fibroblast growth factor, synthetic tissue scaffold, treated allograft scaffold, xenograft tissue scaffold, stem cell, and any combination thereof.

20. The method of claim 13, wherein said step of increasing the localized perfusion of at least the portion of the intravertebral vasculature by inducing angiogenesis comprises administering at least one angiogenic factor by injection into or through a pedicle.

\* \* \* \* \*